United States Patent
West, Jr. et al.

(10) Patent No.: US 6,679,889 B1
(45) Date of Patent: Jan. 20, 2004

(54) APPARATUS AND METHODS FOR INDEPENDENTLY CONDITIONING AND PRETENSIONING A PLURALITY OF LIGAMENT GRAFTS DURING JOINT REPAIR SURGERY

(75) Inventors: Hugh S. West, Jr., Salt Lake City, UT (US); John R. West, Salt Lake City, UT (US)

(73) Assignee: HS West Investments, LLC, Salt Lake City, UT (US)

(*) Notice: Subject to any disclaimer, the term of this patent is extended or adjusted under 35 U.S.C. 154(b) by 242 days.

(21) Appl. No.: 09/711,488

(22) Filed: Nov. 13, 2000

(51) Int. Cl.$^7$ .................................................. A61F 2/38
(52) U.S. Cl. ........................ 606/88; 606/53; 606/62; 606/63; 606/72; 606/73; 606/86; 623/13.11; 623/13.12; 623/13.13; 623/13.14
(58) Field of Search ........................... 606/53, 54, 57, 606/60, 63, 68, 72, 73, 86, 88, 96, 102; 623/13.11–13.17; 128/898

(56) References Cited

U.S. PATENT DOCUMENTS

| | | |
|---|---|---|
| 3,896,500 A | 7/1975 | Rambert et al. |
| 4,301,551 A | 11/1981 | Dore et al. |
| 4,400,833 A | 8/1983 | Kurland |
| 4,467,478 A | 8/1984 | Jurgutis |
| 4,590,928 A | 5/1986 | Hunt et al. |
| 4,597,766 A | 7/1986 | Hilal et al. |
| 4,605,414 A | 8/1986 | Czajka |
| 4,649,916 A | 3/1987 | Frimberger |
| 4,668,233 A | 5/1987 | Seedhom et al. |
| 4,712,542 A | 12/1987 | Daniel et al. |
| 4,739,751 A * | 4/1988 | Sapega et al. ............ 128/92 V |
| 4,744,793 A | 5/1988 | Parr et al. |
| 4,772,286 A | 9/1988 | Goble et al. |
| 4,773,417 A | 9/1988 | Moore et al. |
| 4,834,752 A | 5/1989 | Van Kampen |
| 4,870,957 A | 10/1989 | Goble et al. |
| 4,922,897 A | 5/1990 | Sapega et al. |
| 4,927,421 A | 5/1990 | Goble et al. |
| 4,950,270 A | 8/1990 | Bowman et al. |
| 4,950,271 A * | 8/1990 | Lewis et al. ............... 606/102 |
| 4,969,895 A | 11/1990 | McLeod et al. |
| 4,997,433 A | 3/1991 | Goble et al. |
| 5,037,426 A | 8/1991 | Goble et al. .............. 606/96 |
| 5,071,420 A | 12/1991 | Paulos et al. |
| 5,108,433 A | 4/1992 | May et al. |
| 5,129,902 A | 7/1992 | Goble et al. |
| 5,139,520 A | 8/1992 | Rosenberg |

(List continued on next page.)

Primary Examiner—Linda C. M. Dvorak
Assistant Examiner—Ahmed M Farah
(74) Attorney, Agent, or Firm—Workman Nydegger

(57) ABSTRACT

Apparatus and methods for conditioning and pre-tensioning soft tissue grafts during joint repair surgery, such as during repair of the anterior cruciate ligament (ACL). The inventive apparatus is advantageously adapted and configured so as to enable a surgeon to independently apply a desired tensile load onto individual strands of a multiple-stranded soft tissue graft, such each of a pair of ham strings. The inventive methods advantageously ensure that each strand of a multiple-strand soft tissue graft is adequately tensioned so as to both "condition" the graft to prevent subsequent stretching, relaxation or elongation following surgery, which can destabilize the joint, and pre-tension each strand of the graft to a desired amount so that each significantly contributes to the strength and stability of the joint, thus resulting in a stronger and more durable joint. The inventive tensioning device is advantageously equipped with structure for fastening or otherwise attaching the device to a patient's limb during the conditioning and pre-tensioning procedure. It has multiple adjustable tension applicators that can be independently manipulated so as to independently apply a desired tensile load onto one or more strands of the soft tissue graft attached to each adjustable tension applicator.

21 Claims, 15 Drawing Sheets

FIG. 3G

U.S. PATENT DOCUMENTS

| | | |
|---|---|---|
| 5,147,362 A | 9/1992 | Goble |
| RE34,293 E | 6/1993 | Goble et al. |
| RE34,762 E | 10/1994 | Goble et al. |
| 5,507,750 A * | 4/1996 | Goble et al. ............... 606/102 |
| 5,562,668 A | 10/1996 | Johnson ..................... 606/72 |
| 5,630,820 A | 5/1997 | Todd ......................... 606/90 |
| 5,713,897 A * | 2/1998 | Goble et al. ................. 606/53 |
| 5,935,130 A | 8/1999 | Kilpela et al. |
| 5,964,764 A | 10/1999 | West, Jr. et al. ............. 606/72 |
| 5,980,473 A | 11/1999 | Korakianitis et al. ....... 606/587 |
| 6,001,106 A * | 12/1999 | Ryan et al. ................. 606/102 |
| 6,036,694 A | 3/2000 | Goble et al. ................. 606/72 |
| 6,171,310 B1 | 1/2001 | Giordano et al. |
| 6,279,415 B1 * | 8/2001 | Chance et al. ......... 74/501.5 R |
| 6,364,885 B1 | 4/2002 | Kilpela et al. |

\* cited by examiner

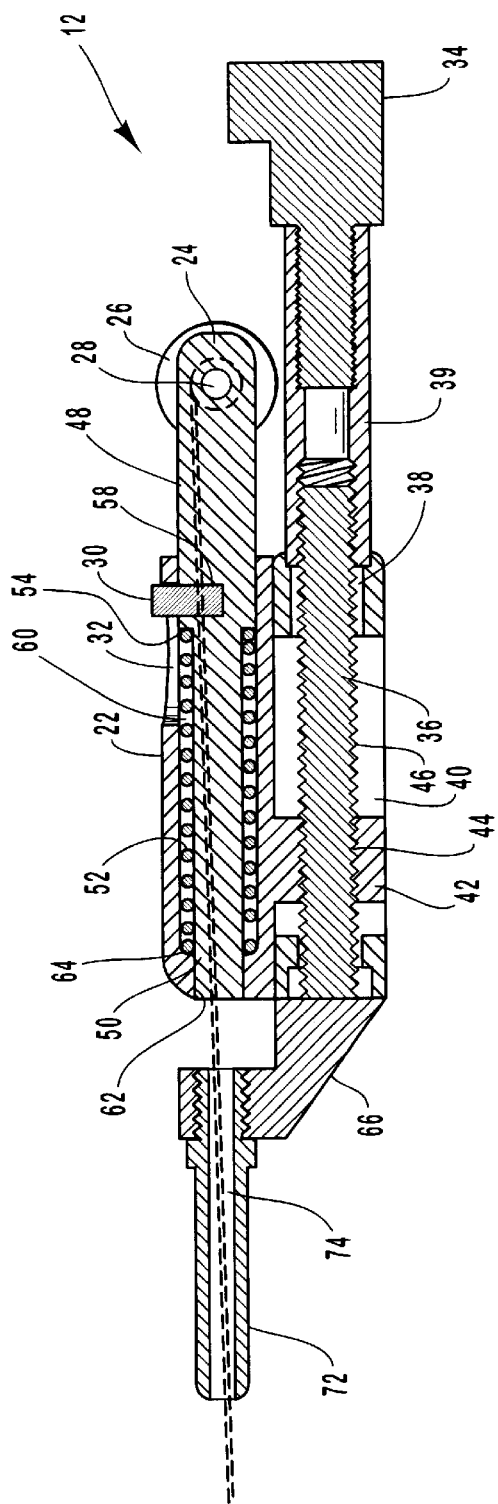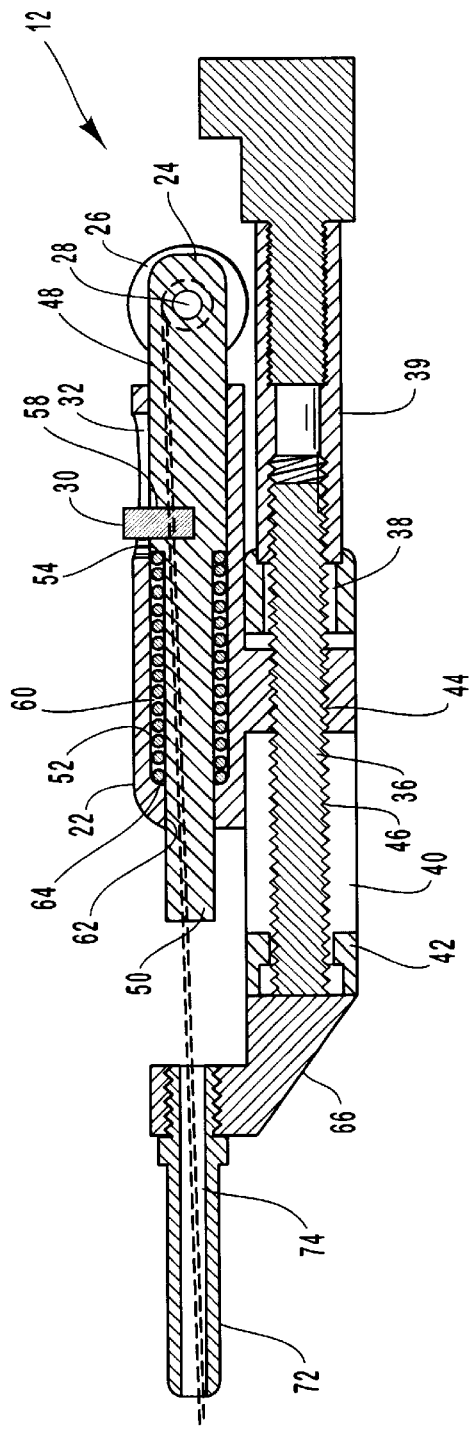

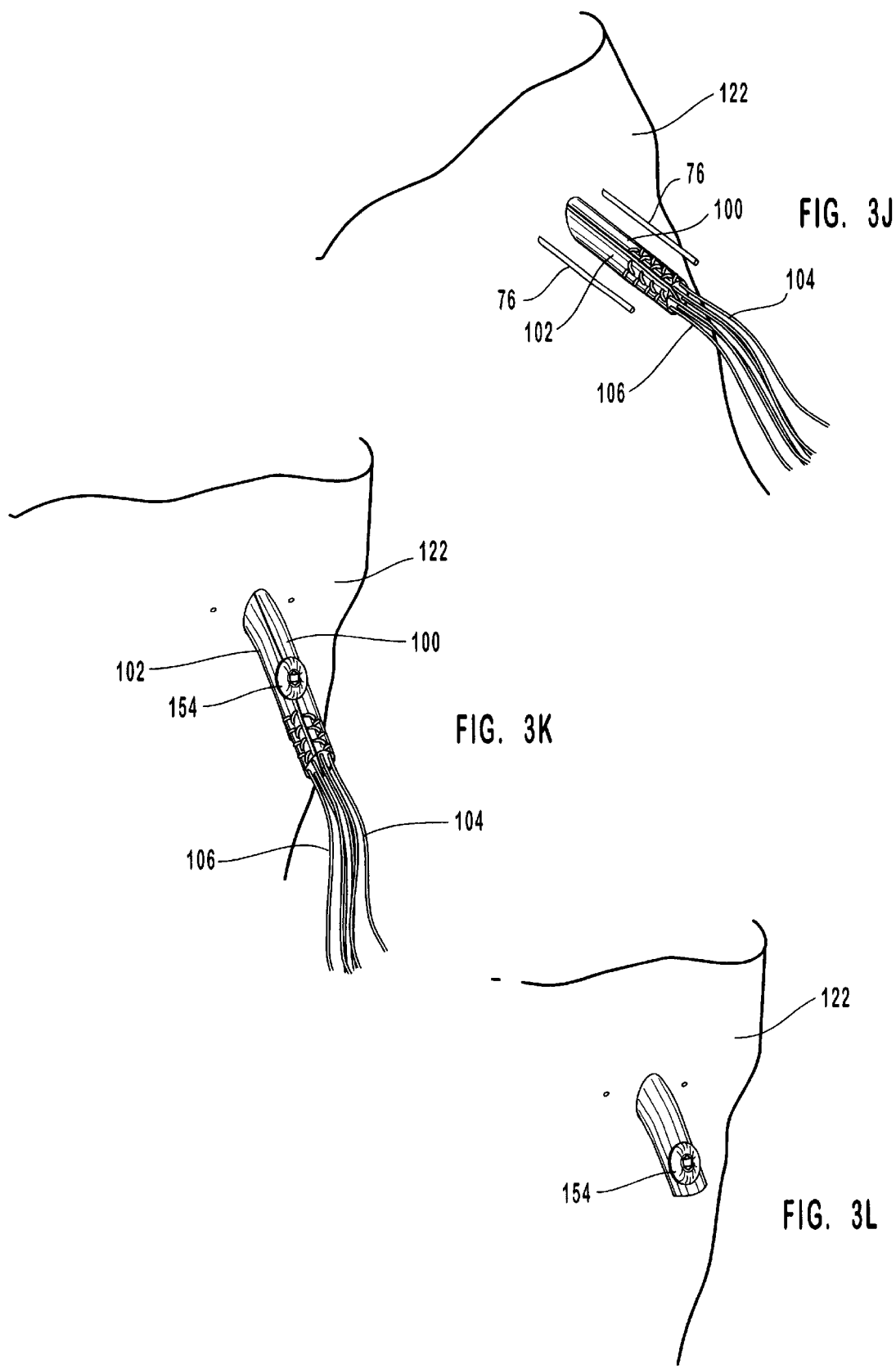

APPARATUS AND METHODS FOR INDEPENDENTLY CONDITIONING AND PRETENSIONING A PLURALITY OF LIGAMENT GRAFTS DURING JOINT REPAIR SURGERY

BACKGROUND OF THE INVENTION

1. The Field of the Invention

The present invention is in the field of joint repair surgery, such as reconstruction of the anterior cruciate ligament (ACL). More particularly, the invention is in the field of tensioning devices for conditioning and pre-tensioning sutures attached to soft tissue grafts used in joint repair procedures, such as sutures independently attached to a pair of ham string grafts. The invention is able to independently condition and pre-tension each soft tissue graft individually.

2. The Relevant Technology

Injuries to joints, specifically the knee, are quite common, particularly when one engages in vigorous sporting activities. A common injury is a rupture or tear of the anterior cruciate ligament (ACL), which is the primary ligament responsible for holding the knee joint together and which keeps it from slipping out of joint or dislocating. An unrepaired ruptured or torn ACL can cripple, and would most certainly limit physical activity of, the person suffering a ruptured or torn ACL. Absent reconstruction of the ACL, such injuries would likely be the end of professional sports careers and would prevent ordinary people from enjoying an active life involving sports and like recreation.

Improvements in surgical procedures have made ACL reconstruction procedures more successful and, hence, more common. In general, an ACL reconstruction procedure involves taking a soft tissue graft from another part of the body, such as the patellar tendon or the hamstrings, and attaching it at both ends through a hole drilled through the two bones that make up the knee joint: the femur and the tibia. When secured in place, the soft tissue graft will mimic and, hence, take the place of, the ACL itself. This soft tissue graft holds the femur and tibia together to make the joint more stable, but is flexible enough to allow for normal joint movements (i.e., flexion and extension).

Graft tension in ACL reconstruction has been recognized as an important factor in the clinical outcome of the ACL reconstruction procedure. In other words, grafts that are too loose may be unstable while grafts that are too tight may greatly restrict motion of the knee. Recent interest in graft tension and scientific work on the subject have raised the demand for quality instruments that will assist the surgeon in more effectively fixing ligament grafts under known tension.

Publications in the past few years have emphasized the need for adequate tensioning of the graft. These include Markolf et al., "Biomechanical Consequences of Replacement of the Anterior Cruciate Ligament With a Patellar Ligament Allograft. Part Two: Forces in the Graft Compared with Forces in the Intact Ligament," *J. Bone Joint Surg. Am.*, 78:11, 1728–34 (November 1996); Tohyama et al., "Significance of Graft Tension in Anterior Cruciate Ligament Reconstruction. Basic background and clinical outcome," *Knee Surg. Sports Traumatol. Arthroscopy*, 6 Suppl. 1, S30-7 (1998); Andersen et al., "Review on Tension in the Natural and Reconstructed Anterior Cruciate Ligament," *Knee Surg. Sports Traumatol. Arthroscopy*, 2:4, 192–202 (1994); Yasuda et al., "Effects of Initial Graft Tension on Clinical Outcome After Anterior Cruciate Ligament Reconstruction. Autogenous Doubled Hamstring Tendons Connected in Series of Polyester Tapes," *Am. J Sports Med.*, 25:1, 99–106 (January 1997). For purpose of disclosure, the foregoing publications are incorporated herein by specific reference.

While much of the focus has been directed to the issue of under tensioning, which typically results in knees that are less stable than normal, application of too much tension may in theory also have an adverse effect by constraining the joints or causing increased pressure on articular surfaces.

A recent study by Hamner et al. has added to the understanding of graft tension by demonstrating that unequal tension in the individual strands of the soft tissue graft can result in significant losses in total graft strength and stiffness. Hamner et al., "Hamstring Tendon Grafts for Reconstruction of the Anterior Cruciate Ligament: Biomechanical Evaluation of the Use of Multiple Strands and Tensioning Techniques," *J. Bone Joint Surg. Am.*, 81:4, 549–57 (April 1999). Hamner et al. studied whether tensioning the soft tissue strands by hand would result in equalization of the load borne by each strand. Hamner et al. showed that this method was not effective in equalizing the load on the strands, which led to an ultimate graft strength that was not significantly greater than the load of the individual strands taken alone.

Previous work has been done to develop and patent devices that are used to apply a known tension to cruciate ligament grafts. Such devices have typically included simple spring scales that apply a known load to the graft as a whole. E.g., U.S. Pat. No. 4,712,542; U.S. Pat. No. 5,037,426; U.S. Pat. No. Re. 34,762; U.S. Pat. No. 5,713,897; U.S. Pat. No. 5,507,750; and U.S. Pat. No. 5,562,668. For purposes of disclosing mechanisms for applying a known load or tension onto a soft tissue graft, the foregoing patents are incorporated herein by specific reference.

Because none of the foregoing references disclose any method for using these devices to separately tension multiple soft tissue grafts, so as to equalize the stress applied to each, one strand will often be preferentially loaded more than another, thus resulting in disparately conditioned and pre-stressed strands that are not significantly stronger or stiffer than a single strand. More particularly, because hamstrings can have different diameters, simply applying a standard load to both strands simultaneously could result in one graft being subjected to a different material stress than the other graft. Moreover, even in the case of hamstrings or other soft tissue grafts that have the same or substantially the same diameters, inadvertent or unavoidable error by the treating surgeon, such as unequal conditioning of each soft tissue graft, can still lead to uneven loads being borne by each individual graft. Regardless of the causes for unequal application of material stress to each of the individual soft tissue grafts, the "tighter" graft (or graft with higher material stress) will reach the failure point first, thereby causing a lower load to failure for the composite graft.

In view of the foregoing, it would be an improvement in the art of joint repair to provide apparatus and methods for independently conditioning and pre-tensioning individual soft tissue graft strands, such as a pair of hamstrings used in an ACL reconstruction procedure.

It would be an additional improvement in the art to provide apparatus and methods for conditioning and pre-tensioning individual graft strands so that each graft strand substantially contributed to the overall strength and stability of the repaired joint.

It would yet be an advancement in the art if such apparatus and methods for conditioning and pre-tensioning individual graft strands could equalize the otherwise unequal conditioning and pre-tensioning of the individual graft strands that might occur, for example, by strands of different diameters or stiffness, or through inadvertent or unavoidable surgical error, such as failure to tie the sutures in a manner so that each graft strand is tensioned equally.

Moreover, it would be an advancement in the art to provide an improved anchor device that could be used in conjunction with such apparatus and methods, which allowed for the independent tensioning of sutures attached to individual soft tissue graft strands, and which could be manipulated after independently tensioning the sutures so as to subsequently lock the sutures in place so as to reliably secure each of the soft tissue graft strands to the bone at a desired tension.

Such apparatus and methods for independently conditioning and pre-tensioning multiple ligament grafts are disclosed and claimed herein.

SUMMARY AND OBJECTS OF THE INVENTION

The present invention encompasses apparatus and methods for independently tensioning a plurality of soft tissue grafts during joint repair procedures, such as in procedures to replace or augment the anterior cruciate ligament (ACL). Because of the importance pre-tensioning soft tissue grafts a predetermined amount, but because of the tendency of soft tissue grafts to relax or stretch after being implanted, it is often necessary to "condition" such grafts prior to anchoring the grafts in place. Soft tissue grafts can be "conditioned" by applying a tensile load for a sufficient amount of time order to prevent further stretching or relaxation of the tissue graft over time after being implanted. In addition to conditioning, it is also generally desirable to pre-stress (or pre-tension) the soft tissue grafts in order to ensure a desired degree of joint stability and strength. Thus, both conditioning and pre-tensioning are important procedures which ensure the success of the joint repair surgery.

Grafts are advantageously "conditioned" prior to being pre-tensioned in order to take the "play" out of the system. Conditioning assists in tightly seating the graft within the bone tunnel and also assists in fully seating the sutures. Only after all of the play has been taken out of the system can the individual grafts be reliable pre-stressed to a desired degree. Attempting to apply a desired amount of material stress to a graft that has not been adequately conditioned typically results in a decay or diminution of actual material stress born by the graft over time. This may lead to long-term instability of the joint.

A predetermined amount of material stress is advantageously applied to the soft tissue grafts in order to yield a joint having a desired amount of stability and stiffness. Inadequately tensioned soft tissue grafts often yield a joint that is not adequately stable or which is too loose, thus being far more prone to subsequent injury and possible rupture of the tissue grafts. However, unless each strand of a multiple strand graft bears approximately the same magnitude of material stress, the strand that initially bears the highest material stress will reach the failure point and rupture first when the joint is subjected to high stress. Subsequently, the graft initially bearing less material stress will then bear all the stress and be more prone to failure since it will be acting on its own to hold the joint together. In short, a soft tissue graft that includes multiple strands that initially bear differing amounts of material stress results in a joint that is both more elastic and which will have a significantly lower composite load to failure point.

Notwithstanding the important of ensuring that each strand of a multiple strand tissue graft are pre-tensioned so as to bear approximately the same material stress, it has heretofore been very difficult to ensure equal, or substantially equal, conditioning and pre-stressing of each strand. As a result, it has heretofore been difficult to ensure that each of the strands contributes equally and simultaneously to the strength and stiffness of the joint.

The present invention proposes novel apparatus and methods to solve the problems associated with the inability to independently condition and pre-tension each strand of a multiple-strand soft tissue graft. The tensioning devices according to the present invention may be configured to apply a desired amount of tension or load to single- or multi-stranded grafts. In a preferred embodiment, the inventive apparatus comprises a tensioning device that includes a plurality of separate adjustable tension applicators (e.g., two) capable of independently applying a desired level of tension to each of the plurality (e.g., two) of soft tissue grafts used in the joint repair surgery. The tensioning device further includes attachment means for removably attaching the device to a patient's bone or limb during the surgical procedure.

An advantage of the inventive tensioning device is the ability to pre-condition the graft after implantation at one end but before fixation. In the case of an ACL reconstruction procedure, because the graft is attached to the tibia near the fixation site, the graft can be tensioned and conditioned by repeatedly flexing and extending the patient's knee under load to remove any laxity or looseness in the graft construct.

The proposed device is advantageously free-standing on the tibia, which can free the surgeon's hands to set knee flexation angle and fix the distal end of the graft while monitoring tension. The device will also be able to sustain a load on the graft for static loading that will help stretch the graft before fixation.

In one embodiment, each adjustable tension applicator of the tensioning device includes attachment means for securing one or more sutures attached to the soft tissue graft and an adjustable biasing mechanism (e.g., a spring-loaded mechanism) capable of applying a measured tensile load to the sutures and associated soft tissue graft. The adjustable biasing mechanism further includes an immobile base or block, a cylinder block or module slidably disposed on the immobile base, a tensioning piston slidably disposed within a portion of the cylinder block, a biasing spring communicating between the cylinder block and the tensioning piston, and a rotatable adjustment knob threadably attached to the slidable cylinder block, which, upon turning, selectively urges the cylinder block towards or away from the tensioning piston so as to selectively compress or extend the biasing spring and thereby increase or decrease the load applied by the biasing spring onto the tensioning piston.

The means for securing the one or more sutures to the tensioning pistons may advantageously include a suture attachment wheel rotatably connected to each tensioning piston. Free rotation of the suture attachment wheel ensures equal tension being applied to each side of a looped suture strand.

While the tensioning device is in use, outward movement of the tensioning piston relative to the slidable cylinder block as the compressive force applied by the biasing spring is restricted by the countervailing inward tension exerted by the soft tissue graft attached to the tensioning piston by means of the sutures. Thus, during conditioning and subsequent pre-tensioning of the soft tissue graft, the tensioning piston may only move a few millimeters, or less, as the soft tissue graft is stretched. Turning of the adjustment knob causes the slidable cylinder block to move either towards or away from the essentially immobilized tensioning piston. Movement of the cylinder block towards the tensioning piston causes the biasing spring to become progressively compressed, thus increasing the outward, or compressive, force exerted by the spring onto the piston. Likewise, movement of the cylinder block away from the piston progressively decompresses the biasing spring, thus decreasing the compressive force exerted by the spring onto the piston.

The magnitude of compressive force exerted by the biasing spring onto the piston is essentially equivalent to the magnitude of the tensile force exerted onto the soft tissue graft by the tensioning piston. Because the amount of compressive force exerted by a spring is directly related to the distance that the spring has been compressed, the compressive load exerted by the spring onto the tensioning piston, and the tensile load exerted by the tensioning piston onto the soft tissue graft, can be indirectly measured by measuring the distance the spring has been compressed. Thus, the adjustable biasing mechanism may advantageously be equipped with a gauge or other means for measuring the magnitude of spring compression so as to indirectly measure the amount of tensile load being exerted on the soft tissue graft during conditioning and pre-tensioning.

Notwithstanding the foregoing, one will readily appreciate, in view of the disclosure herein, that inventive devices according to the invention are not limited to any particular mechanism for performing the individual and separate tasks of independently tensioning a plurality of strands of a soft tissue graft. The mechanisms described herein are but illustrative and exemplary. For example, the tension loading function could alternatively be provided by a variety of simple scales, such as tension springs, compression springs, torsion springs or electronic transducers. In addition a variety of electronically actuated and measured tensioning devices are certainly within the scope of the invention so long as they are capable of independently tensioning separate soft tissue grafts. Examples include a strain gauge, a rotary guage, an LVDT and the like.

The tensioning device can potentially be used to monitor isometry and measure tension in a single strand of a soft tissue graft. The current design could also be altered in order to incorporate additional adjustable tension applicators that can exert and measure tension in as many stands as a surgeon might choose to include in the soft tissue graft.

In a preferred method for carrying out the procedures according to the present invention, two soft tissue grafts are taken from the patient, such as from the ham strings or patellar tendon, drawn through holes bored through the femur and tibia according to known surgical procedures, and attached to the femur according to known surgical procedures. Sutures are attached to the strands of the soft tissue graft at an appropriate point during the implantation procedure using known methods. The end of the soft tissue graft opposite the sutures is passed through holes bored through the tibia and femur and secured to the femur using known surgical procedures. The sutures and a portion of the graft extend out of an access hole in the patient's leg near the hole in the tibia.

Thereafter a tensioning device capable of separately applying a tension to each of the soft tissue grafts is provided, an example of which is the preferred device described more fully herein. The tensioning device will advantageously include two or more adjustable tension applicators corresponding to the two or more soft tissue graft strands, respectively. The tensioning device is then attached to the patient's bone or limb by means of guide pins drilled into the bone, or some other appropriate manner (i.e., by means of a belt or band wrapped around the patient's leg), followed by attaching the sutures associated with one of the soft tissue graft strands to one adjustable tension applicator and attaching the other soft tissue strand to the other adjustable tension applicator. In the case of a modular tensioning device, the module responsible for securing the tensioning device to the patient's tibia is advantageously attached to the leg first. Thereafter, the module responsible for applying the tensile load to the soft tissue grafts is attached to the attachment module. Of course, a single, non-modular unit may also be employed.

After the sutures have been secured to the tensioning device, the tensioning device is used to independently apply a desired tensile load to each of the two soft tissue graft strands. This may be done, for example, by tightening the tension knobs of each adjustable tension applicator described above so as to compress the biasing spring and thereby apply a corresponding compressing force onto each tensioning piston, which is essentially equal to the magnitude of the tensile load exerted by the tensioning piston onto the soft tissue graft strand.

Thereafter, the joint (e.g., the knee) is advantageously "cycled" by the treating physician, i.e., flexed and extended between zero and 90° a number of times (e.g., 25 repetitions) in order to assist in conditioning the soft tissue graft strands and also to test the joint stability. The process of increasing the tensile load applied to each of the soft tissue graft strands by the tensioning device followed by cycling of the joint is repeated until a desired level of conditioning, prestressing and associated joint stability and strength are achieved. When negligible losses in joint stability are observed, the soft tissue graft is secured to the bone (e.g., the tibia) by appropriate anchoring means known in the art, or by means of the novel implantable anchor device disclosed herein.

An example of anchoring means known in the art is an interference screw, which is screwed directly into the hole in the patient's bone (e.g., the tibia) through which the soft tissue graft is passed by means of a driver. After the interference screw has been screwed in place, the driver and tensioning device are removed. If guide pins are used to secure the tensioning device to the person's leg, these are also removed. The remaining portion of the soft tissue grafts that extend beyond the bone may be secured to the outer surface of the bone by securing means known in the art, e.g., a spiked washer, staple or post in order to reinforce fixation of the graft. The graft is then trimmed to remove the sutures, and the incision in the leg closed.

In an alternative embodiment, a novel implantable anchor device may be employed to secure the soft tissue graft to the tibia or other bone. An exemplary anchor includes a cylindrical outer sheath having a cylindrical outer wall and a generally cylindrical bore therethrough, and a corresponding locking core or shaft used to lock the sutures into place once the conditioning and pre-tensioning procedure has been completed. The circumference of the outer sheath is selected to fit within the hole bored through the tibia or other bone.

The bottom part of the outer sheath, or the part of the sheath which faces the bone, includes a plurality of suture holes disposed near the outer edge of the sheath adjacent to the cylindrical outer wall. The suture hole permits passage therethrough of the individual strands of the sutures attached to the soft tissue grafts. The outer sheath, inward of the suture holes, may be closed or include a hole through center of the sheath bottom face. A hole permits the passage therethrough of an interference screw, post, or other device capable of urging the soft tissue graft against the walls of the hole through the bone to promote faster adhesion thereto. The use of an interference screw also strengthens the fixation of the graft to the bone.

The top part of the sheath, or the part of the sheath facing away from the bone, includes a lip or other protrusion extending laterally from the edge of cylindrical outer wall. When the anchor device is placed into the bore within the tibia or other bone, the lip or other protrusion advantageously overlaps the outer surface of the bone, thus acting as a stop to hold the anchor device in a desired location. The inward tension exerted by the soft tissue graft onto the sutures effectively pulls the lip or protrusion against the bone, thus reliably locking the anchor device against the bone.

The locking core is capable of sliding into and out of the outer sheath, but has a slightly tapered outer wall so that it can form an increasingly tighter press fit with the inner wall of the outer sheath as it is pressed or forced into the sheath. The locking core is preferably hollow and includes suture passages passing through the bottom edge nearest, and corresponding to, the suture holes of the outer sheath. The suture passages pass approximately longitudinally through the locking core but at an angle so that they exit through the outer wall of the locking core rather than the top edge, or the edge facing away from the outer sheath. In this way, the sutures will pass through the locking core in a manner so that, when the locking core is deployed, the sutures will be tightly pinched between the outer wall of the locking core and the inner wall of the outer sheath. This pinching action prevents the sutures from slipping back into the bone hole, thus maintaining the desired tension on the sutures and associated soft tissue graft strands after conditioning and pre-tensioning of the individual graft strands, as described more fully herein. Prior to deployment of the locking core, the sutures are free to slide inwardly or outwardly as desired relative to the outer sheath and the locking core, which allows the tensioning device to increase or decrease the tensile load applied to the soft tissue graft strands, as desired.

Accordingly, it is an object of the invention to provide apparatus and methods for independently conditioning and pre-tensioning individual soft tissue graft strands, such as a pair of hamstrings used in an ACL reconstruction procedure.

It is an additional object and feature of the invention to provide apparatus and methods for conditioning and pre-tensioning individual graft strands so that each graft strand may substantially contribute to the overall strength and stability of the repaired joint.

It is yet an object of the invention to provide apparatus and methods for conditioning and pre-tensioning individual graft strands that can equalize the otherwise unequal conditioning and pre-tensioning of the individual graft strands that might occur, for example, by strands of different diameters or stiffnesses, or through inadvertent or unavoidable surgical error, such as failure to tie the sutures in a manner so that each graft strand is tensioned equally.

Moreover, it is an object to provide an improved anchor device that can be used in conjunction with the foregoing apparatus and methods, which allows for the independent tensioning of sutures attached to individual soft tissue graft strands, and which can be manipulated after independently tensioning the sutures so as to subsequently lock the sutures in place and thereby reliably secure each of the soft tissue graft strands to the bone at a desired tension.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 2 is a side cross-sectional view of the tensioning device depicted in FIG. 1 taken along line 2—2.

FIG. 2A shows the tensioning device of FIG. 2 after compression of the biasing spring to increase to tensile load exerted by the tensioning piston.

FIGS. 3A–3L successively illustrate exemplary steps during conditioning and pre-stressing, and mounting of a multiple strand tissue graft within a bone tunnel using the tensioning device of FIG. 1 in combination with an interference screw.

DETAILED DESCRIPTION OF THE PREFERRED EMBODIMENTS

I. INTRODUCTION

Figure 1:
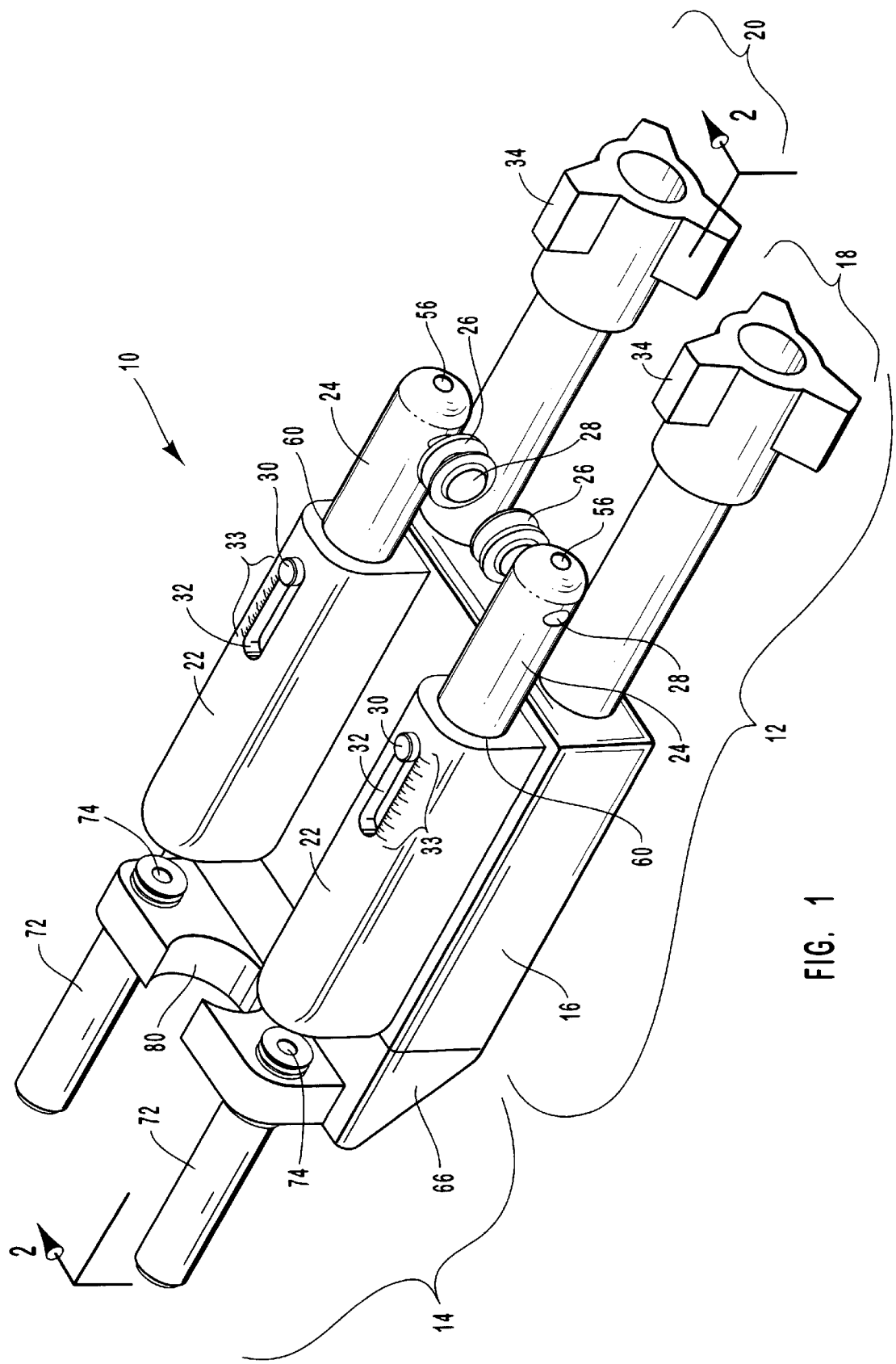
FIG. 1 is a perspective view of a tensioning device according to the invention.

The present invention is directed to apparatus and methods for independently tensioning a plurality of soft tissue grafts (e.g., two) during joint repair procedures, such as in procedures to replace the anterior cruciate ligament (ACL). In order for the soft tissue graft to provide adequate joint stability and provide a predetermined amount of strength, but because of the tendency of many soft tissue grafts (e.g., ham strings) and/or sutures attached thereto to relax after the graft has been implanted, it is often necessary or desirable to "condition" the graft prior to being permanently anchored to the bone. Conditioning is advantageously performed to take the play out of the system and to ensure adequate seating of the graft prior to pre-stressing. It may also be desirable to pre-stress (or pre-tension) the soft tissue graft to provide a predetermined amount of joint stability and strength. Thus, conditioning and pre-tensioning of the soft tissue grafts can help to ensure the success of the surgical procedure.

Where multiple strands of soft tissue are used as the ligament graft, it is often difficult or even impossible using prior-art devices and procedures to ensure equal, or substantially equal, conditioning and pre-tensioning of each strand. Unless each ligament graft is adequately conditioned and pre-tensioned, it is unlikely that each of the soft tissue strands will contribute equally to the strength of the joint. Evidence has shown that the strands that have been inadequately conditioned and pre-tensioned may bear little, if any, of the load applied to the joint during normal use, absent stretching or tearing or the more highly conditioned and pre-tensioned strands. In the case of grafts comprising a pair of hamstring strands, one of which is improperly conditioned and pre-tensioned, the majority of the load will be born by the strand that has been more fully conditioned and pre-tensioned.

Prior apparatus and procedures are only able to apply tension to multiple-stranded grafts as a group, rather than individually. Such procedures often result in one strand being better conditioned and pre-tensioned than the other for at least two reasons. First, unavoidable or inadvertent error in how the sutures are initially tied to the soft tissue grafts may result in the inability to apply an equal load to each of the strands. In other words, one of the sets of sutures attached to one of the soft tissue strands may become taught before the other set or sets of sutures attached to the other soft tissue strand(s), thus resulting in proper conditioning and pre-tensioning of only that strand that is first subjected to the tensile load.

Second, not all ham strings or other soft tissue grafts are of equal cross-section and/or inherent stiffness. Thus, some strands may undergo, or allow for, greater stretching, or "strain", before the desired level of tensile load has been applied to the strand to ensure proper "conditioning" and subsequent pre-tensioning. Strands of greater cross-section may also require being subjected to a higher tensile load to become properly conditioned. The sutures tied to each strand of a multiple-stranded graft may not be equally tight initially before condition, thus possibly requiring greater magnitudes of "strain" (or pulling distance) on different strands to achieve the same degree of conditioning. An apparatus or procedure that is unable to adjust for such variations in tissue graft stiffness or cross-sectional diameter may be incapable of ensuring proper conditioning and subsequent pre-tensioning of each strand of the soft tissue graft. The same is true for the inability to account for inherent variations in initial suture tautness or other systematic or random variations in how the surgeon ties the individual sutures to each soft tissue strand.

The present invention proposes novel apparatus and methods to solve the foregoing problems. More particularly, the inventive apparatus comprises a tensioning device that includes a plurality of separate adjustable tension applicators (e.g., two) capable of independently applying a desired level of tension to each of the plurality (e.g., two) of strands of the soft tissue graft used in the joint repair surgery. The tensioning device further includes attachment means for removably attaching the device to a patient's bone or limb during the surgical procedure.

II. TENSIONING DEVICES USED TO CONDITION AND PRE-TENSION SOFT TISSUE GRAFTS IN JOINT REPAIR PROCEDURES.

An illustrative tensioning device capable of independently conditioning and applying tensioning to two separate soft tissue strands, or groups of strands, is depicted in FIG. 1. In particular, FIG. 1 depicts a tensioning device 10 that is modular, i.e., that includes two separate and detachable substructures or systems, namely a tensioning system 12 and a limb attachment system 14. The tensioning system 12 further includes a pair of adjustable tension applicators capable of independently applying tension to each of a pair of soft tissue strands, or groups of strands. As shown in FIG. 1, the tensioning system 12 includes a tensioning block or module 16. Attached to, or associated with, the tensioning module 16 are a first adjustable tension applicator 18 and a second adjustable tension applicator 20, which are essentially mirror images of each other. Because of this, each of the exemplary first and second adjustable tension applicators 18 and 20 depicted in FIG. 1 may be described in a single detailed description. Of course, it is certainly within the scope of the invention to include additional adjustable tension applicators and/or to vary the design of each adjustable tension applicator as desired.

In order to better understand the mechanical structures and operation of each of the first and second adjustable tension applicators 18 and 20, more particular reference is made to FIGS. 2 and 2A, which are cross-sectional views of second adjustable tension applicator 20 taken along line 2—2 in different stages of applying tension. Cross-reference to FIG. 1 may also be helpful in understanding the interplay between the first and second adjustable tension applicators 18 and 20 and their mechanical structures. Each of the first and second adjustable tension applicators 18 and 20 includes a cylinder block or module 22 and a tensioning piston 24 partially disposed within the cylinder module 22. The cylinder module 22 and tensioning piston 24 are able to slide relative to each other, as will be described more fully below.

In order to attach or otherwise secure each of two sets of sutures respectively attached to each of two soft tissue strands, each tensioning piston 24 further includes a suture attachment wheel 26 attached by means of an axle 28 to the tensioning piston 24. The suture attachment wheel 26 was selected because it is able to rotate, and thereby self-adjust, after the sutures have been tied and looped around the suture attachment wheel 26. This ability to rotate ensures that equal tension is applied to each strand of the suture on either side of the suture attachment wheel 26. It will be appreciated, however, that other attachment means for attaching the sutures to the tensioning piston 24 are within the scope of the invention, including slots, posts, holes, ridges, and the like (not shown).

In order to gauge the amount of tensile load being applied by each of the tensioning pistons 24 to its respective soft tissue graft strand, or group of strands, a tension post 30 attached to the tensioning piston 24 is provided, which extends through, and freely moves within, a tension indicator slot 32 within the cylinder module 22. As will be discussed below, the magnitude of the tensile load being applied to the soft tissue graft strand at any given time will be related to the relative distance that the tension post 30 has moved relative to the cylinder module 22. In actuality, because the tensioning piston 24 is essentially immobile due to the countervailing tension applied by the corresponding soft tissue strand, it is the cylinder module 22 and its associated tension indicator slot 32 that will typically move relative to the tension post 30 as the tensile load applied to the soft tissue graft is increased (Compare FIGS. 2 and 2A). Regardless of which element actually moves, the location of the tension post 30 relative to the tension indicator slot 32 provides the surgeon with an accurate visual indicator of the amount of tensile load being applied by each adjustable tension applicator 18 and 20 to its respective soft tissue graft strand(s) at any given time. In order to provide a more accurate way of determining the exact load being applied, graduations 33 may be provided on the cylinder module 22 at or near the tension indicator slot 32. The graduations 33 may provide any desired measuring standard, such as metric (e.g., Newtons) or English units (e.g., pounds), as well as any desired level of precision.

In order to adjust the amount of tension applied by each adjustable tension applicator 18 or 20, a mechanism for moving the cylinder module 22 either towards or away from the tensioning piston 22 is provided. As seen in FIGS. 2 and 2A, each adjustable tension applicator 18 or 20 includes a tension adjustment knob 34 attached to a tension adjustment bolt 36 in threaded communication with the cylinder module 22. The tension adjustment bolt 36 passes through a pair of bolt holes 38 at the front and back ends of the tensioning block or module 16, respectively. The holes 38 are not threaded and thus allow for free rotation of the tension adjustment bolt 36 without changing the location of the tension adjustment bolt 36 relative to the tensioning module 16. For ease of use, and to conveniently extend the tension adjustment knobs 34 behind or beyond the tensioning pistons 24, knob extenders 39 may be provided as shown in both FIGS. 1 and 2.

Between each of holes 38, the tension adjustment bolt 36 is suspended within a cylinder block guide cavity 40, which holds and guides the cylinder module 22 as it slides back and forth relative to the tensioning block 16 and the tensioning piston 24. More particular, a side tongue or extension 42 extending laterally from the bottom of the cylinder module 22 is able to slide back and forth within the cylinder block guide cavity 40. The side extension 42 of the cylinder module 22 further includes a threaded hole 44 through which passes, and which is in threaded communication with, the tension adjustment bolt 36, which includes corresponding threads 46. The interaction between the adjustment bolt threads 46 and the threaded hole 44 of the cylinder module 22 provides for fine, adjustable movement of the cylinder module 22 either toward or away from the tensioning piston 24 as the surgeon selectively rotates the tension adjustment bolt 36, such as by means of the tension adjustment knob 34.

The degree or magnitude of the movement of the cylinder module 22 per revolution of the tension adjustment bolt 36 is, of course, dependent on the gauge of the threads 46. Increasing the number of threads per unit of length on the adjustment bolt 36 and threaded hole 44 provides for smaller or finer movements of the cylinder module 22 per turn of the adjustment bolt 36. Likewise, decreasing the number of threads per unit of length on the adjustment bolt 36 and threaded hole 44 provides for larger or coarser movements of the cylinder module 22 per turn of the adjustment bolt 36. One of ordinary skill in the art can select a thread gauge in order to provide for a desired magnitude of movement of the cylinder module 22 per turn of the adjustment bolt 36.

As seen in FIGS. 2 and 2A, the tensioning piston 24 further includes a first piston end 48 having a first diameter and a second piston end 50 having a second diameter that is smaller than the diameter of the first piston end 48. A biasing spring 52 is circumferentially disposed around the second piston end 50 and makes abutment with an internal end face 54 of the first piston end 48. As better seen in FIG. 1, the tensioning piston 24 also includes a longitudinal guide pin hole 56 through which a guide pin (to be discussed hereinafter) can pass, if necessary, during attachment of the tensioning device 10 to the patient's limb. The tensioning piston 24 also includes an attachment hole 58 into which the tension indicator pole 30, is mounted.

As stated above, the tensioning piston 24 is slidably disposed within the cylinder module 22. As more particularly seen in FIGS. 2 and 2A, the cylinder module 22 includes an internal cylindrical hollow 60 having a diameter that is complementary to the diameter of the first piston end 48 so as to allow for slidable passage of the first piston end 48 therethrough as the cylinder module 22 is moved either towards or away from the tensioning piston 24. The cylinder module 22 further includes a smaller diameter end hole 62 sized so as to allow for slidable passage of the smaller diameter second piston end 50 therethrough as the cylinder module 22 is moved either towards or away from the tensioning piston 24. The biasing spring 52 that is circumferentially disposed around the smaller diameter second piston end 50 of the tensioning piston 24 makes abutment with an internal end face 64 of the internal cylindrical hollow 60 at the junction with the end hole 62.

Thus, the biasing spring 52 is maintained within the length or volume defined by the internal end face 64 of the internal cylindrical hollow 60, on one end, and the internal end face 54 of the fist piston end 48 of the tensioning piston 24, on the other end. In this way, the biasing spring 52 becomes compressed as the cylinder module 22 is moved towards the tensioning piston 24 (as seen in FIG. 2A), thereby increasing the compressing force applied by the biasing spring 52 onto the tensioning piston 24, which is essentially equal in magnitude to the tensile load applied by the tension piston 24 onto the soft tissue graft attached thereto, such as by way of tissue graft attachment sutures.

The foregoing tensioning system is merely exemplary and not limiting. Although the tensioning piston 24, cylinder module 22 and biasing spring 52 are configured so as to progressively compress the tensioning spring in order to apply increasing force to a soft tissue graft, it would certainly be within the scope of the invention to provide a configuration or alternative tensioning system in which a biasing spring were instead progressively elongated in order to applied increasing force to the soft tissue graft.

In order for the foregoing tensioning system 12 to be conveniently used to independently tension a pair of soft tissue grafts, the tensioning system 12 is advantageously attached to the patient's limb (e.g., the leg below the knee) by means of the limb attachment system 14. As seen in FIGS. 1, 2 and 2A, the limb attachment system 14 includes a limb attachment block or module 66 that is matable with the tensioning block or module 16. In this way, once the attachment module 66 has been attached to the patient's limb, the tensioning system 12 can be conveniently and easily attached to the limb attachment system 14.

Figure 3A:
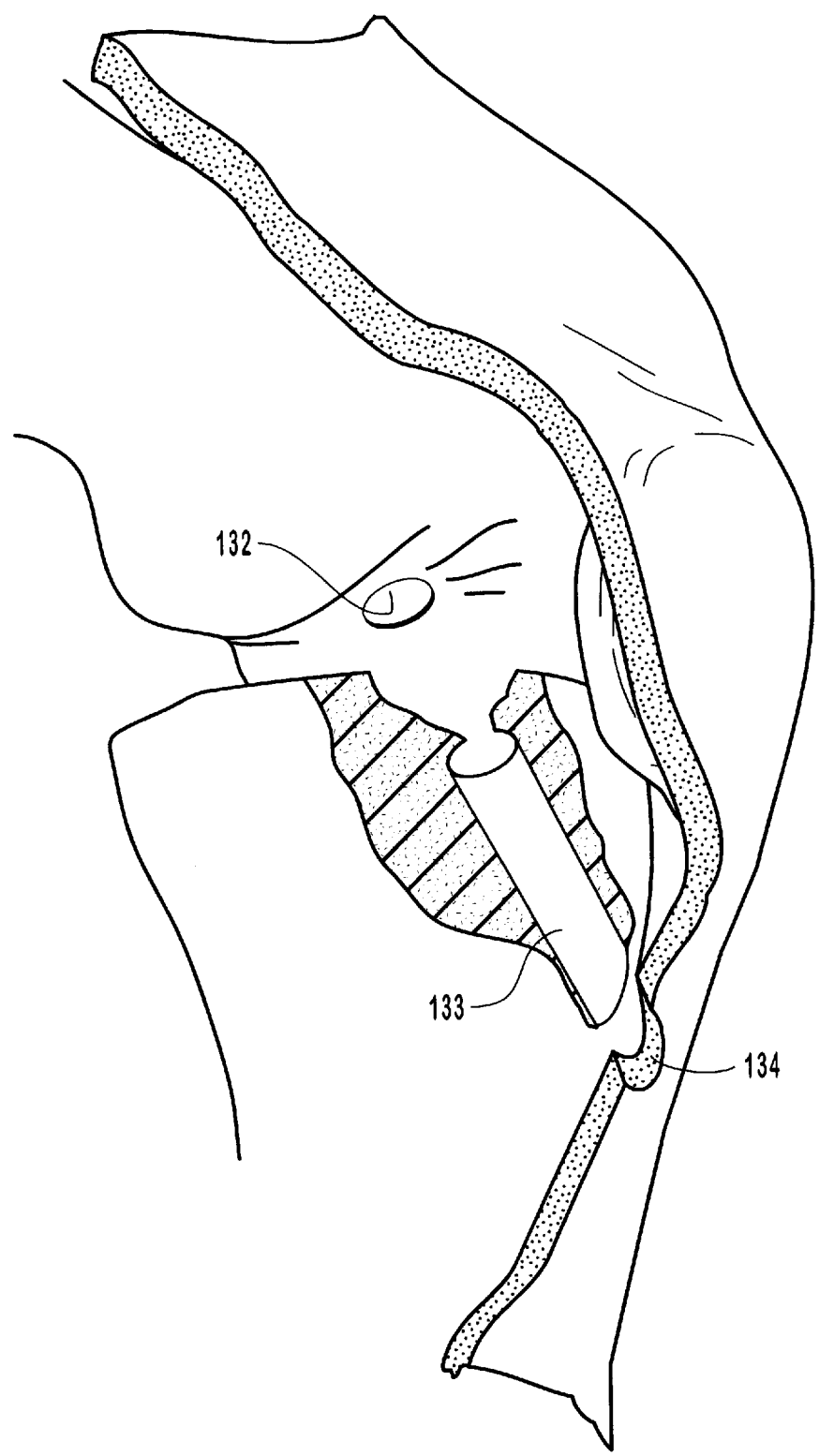
Figure 3B:
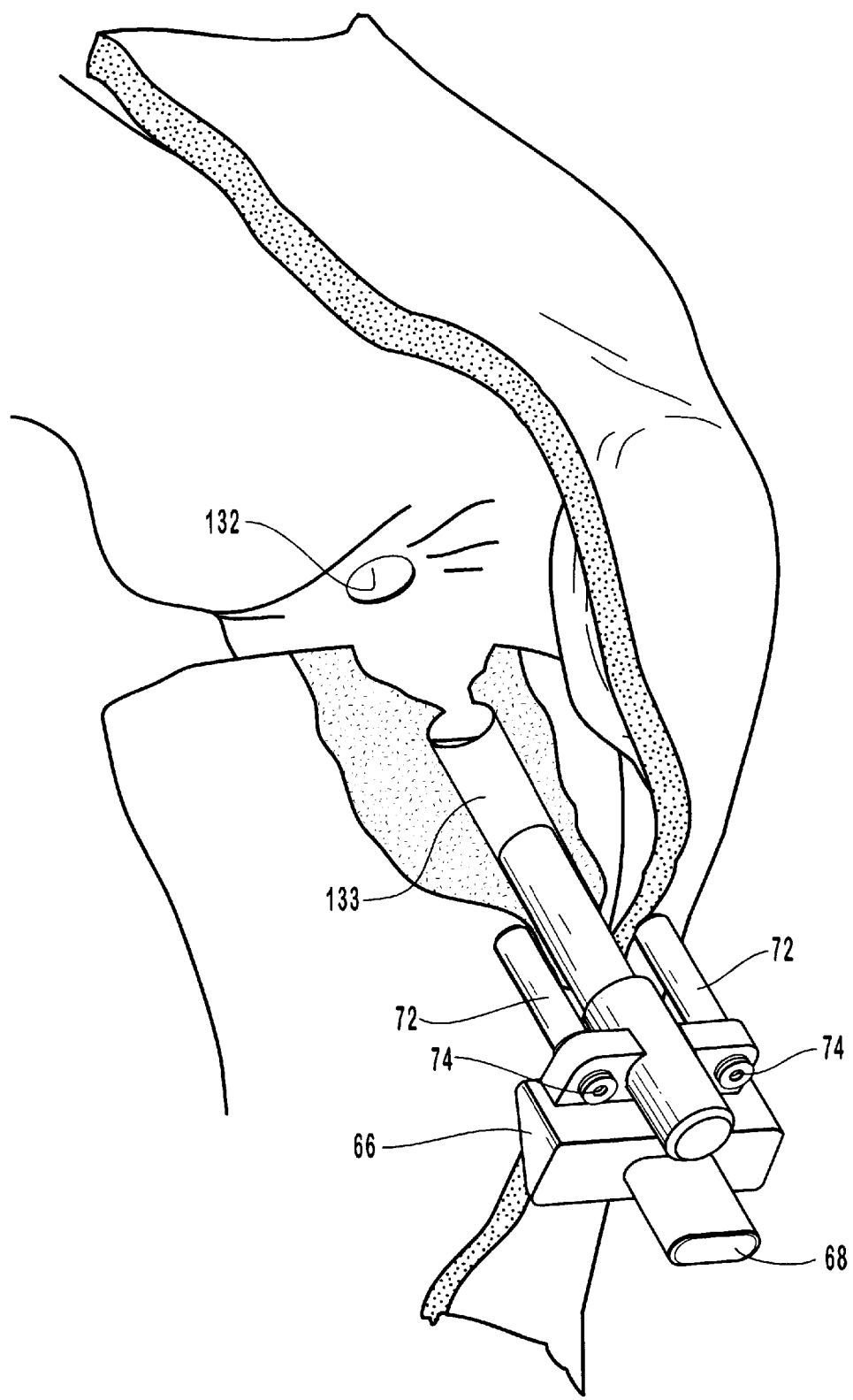
Figure 3C:
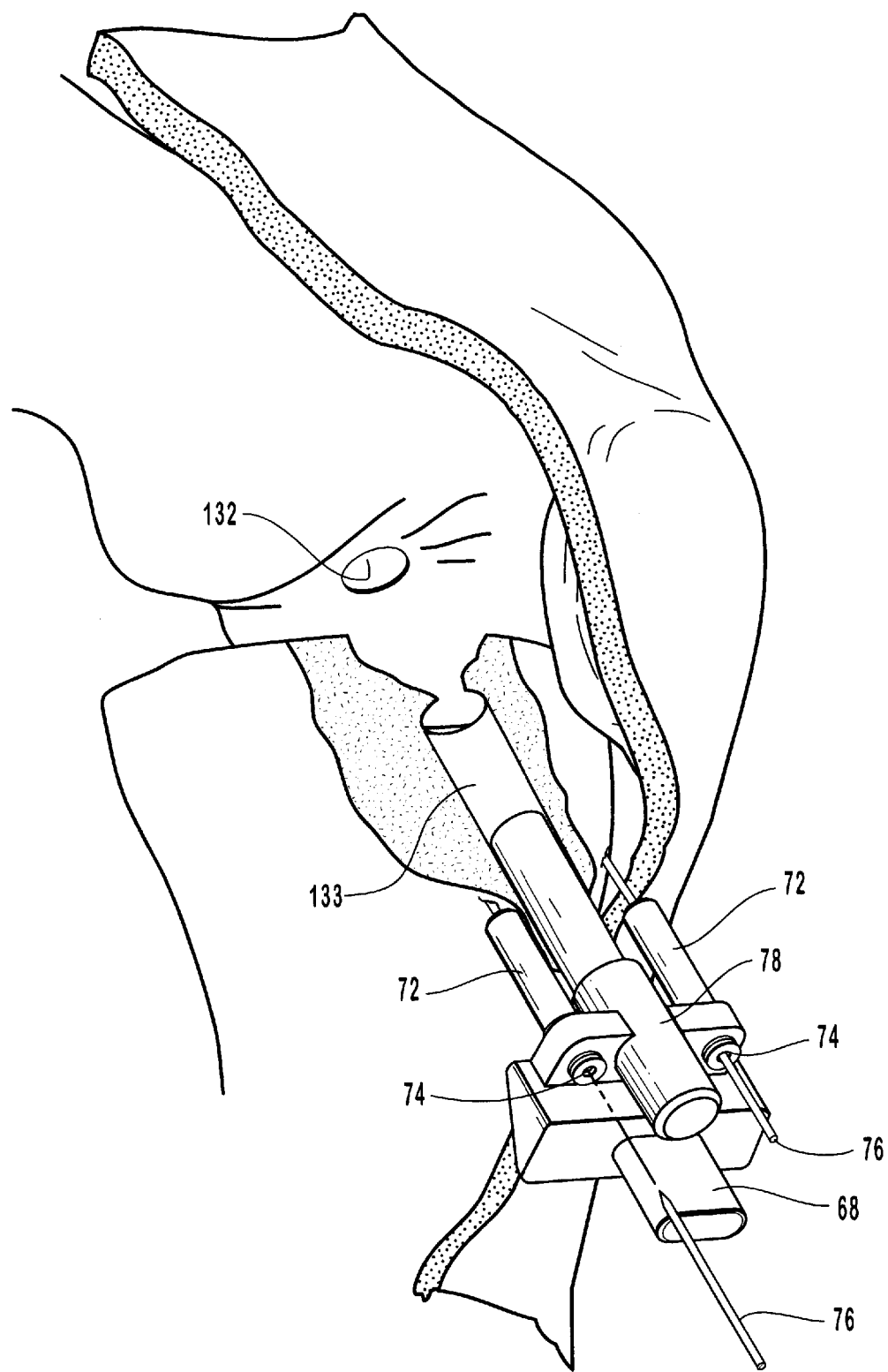
Figure 3D:
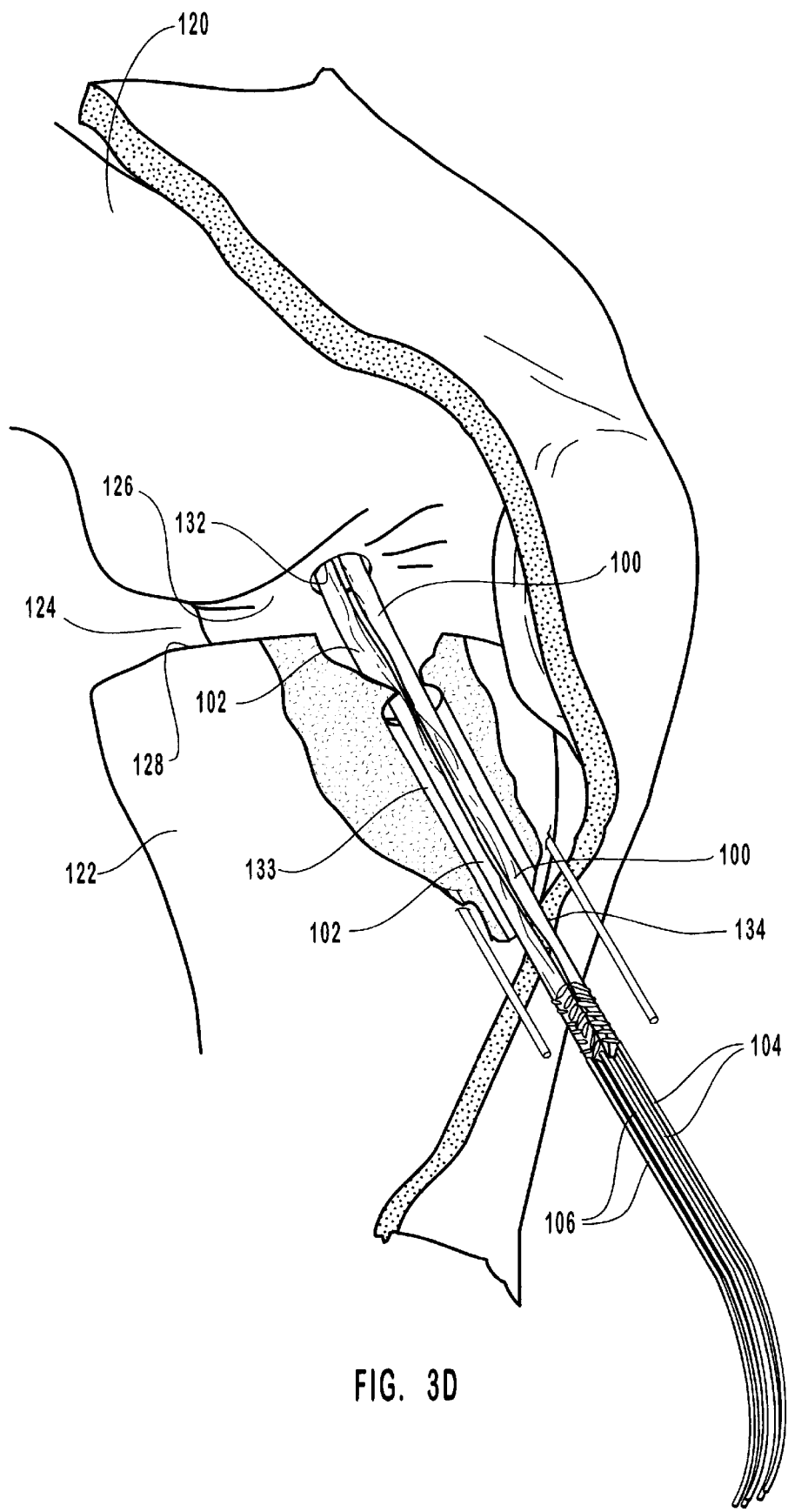
Figure 3E:
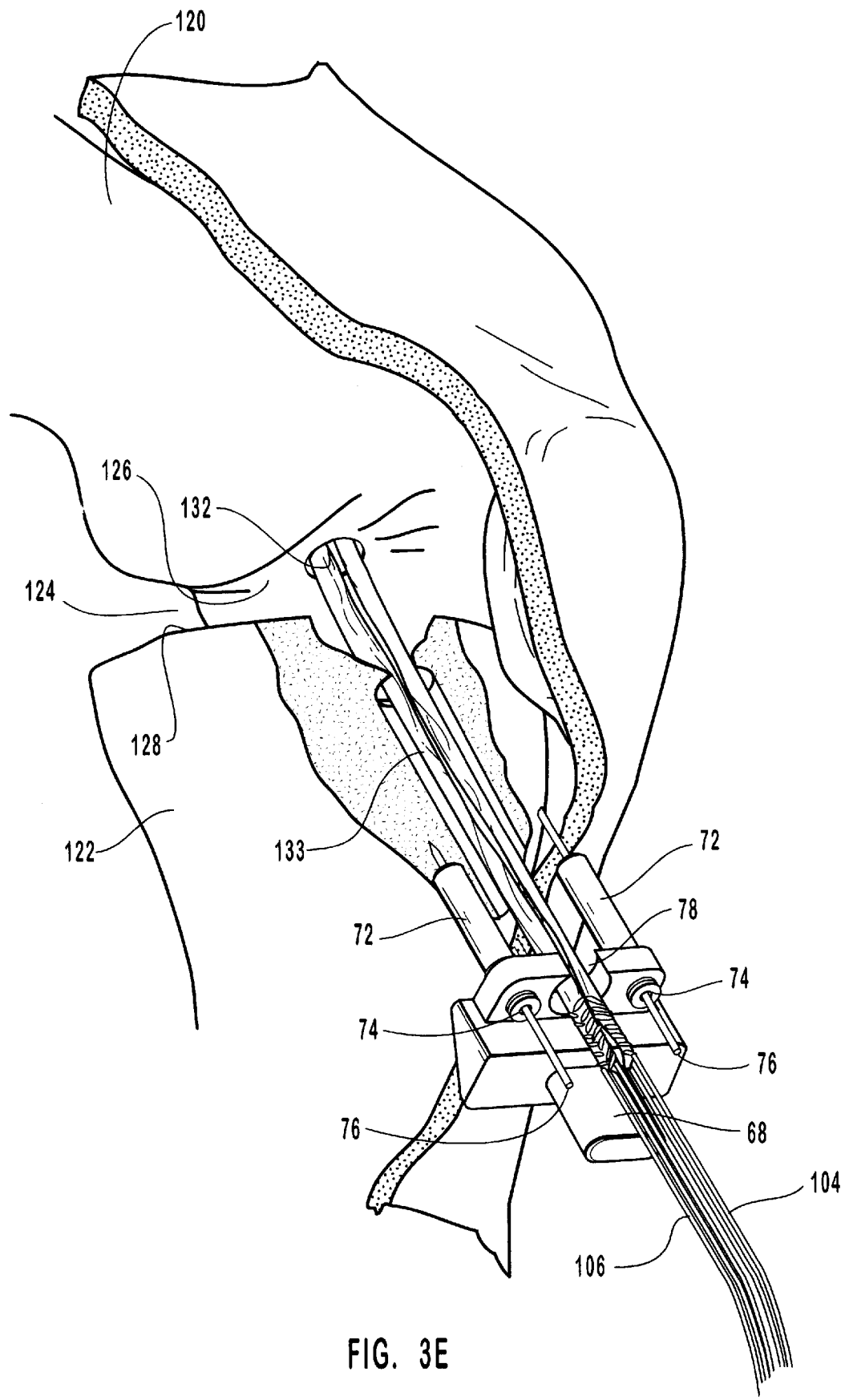
Figure 3F:
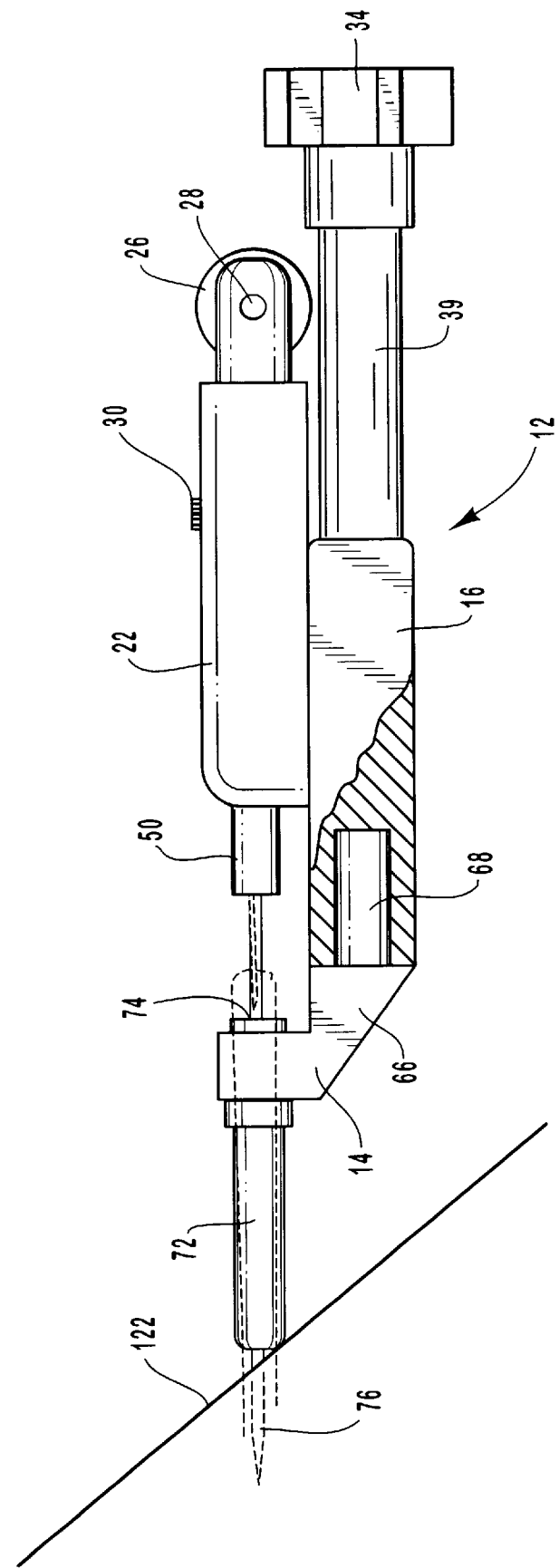
Figure 3G:
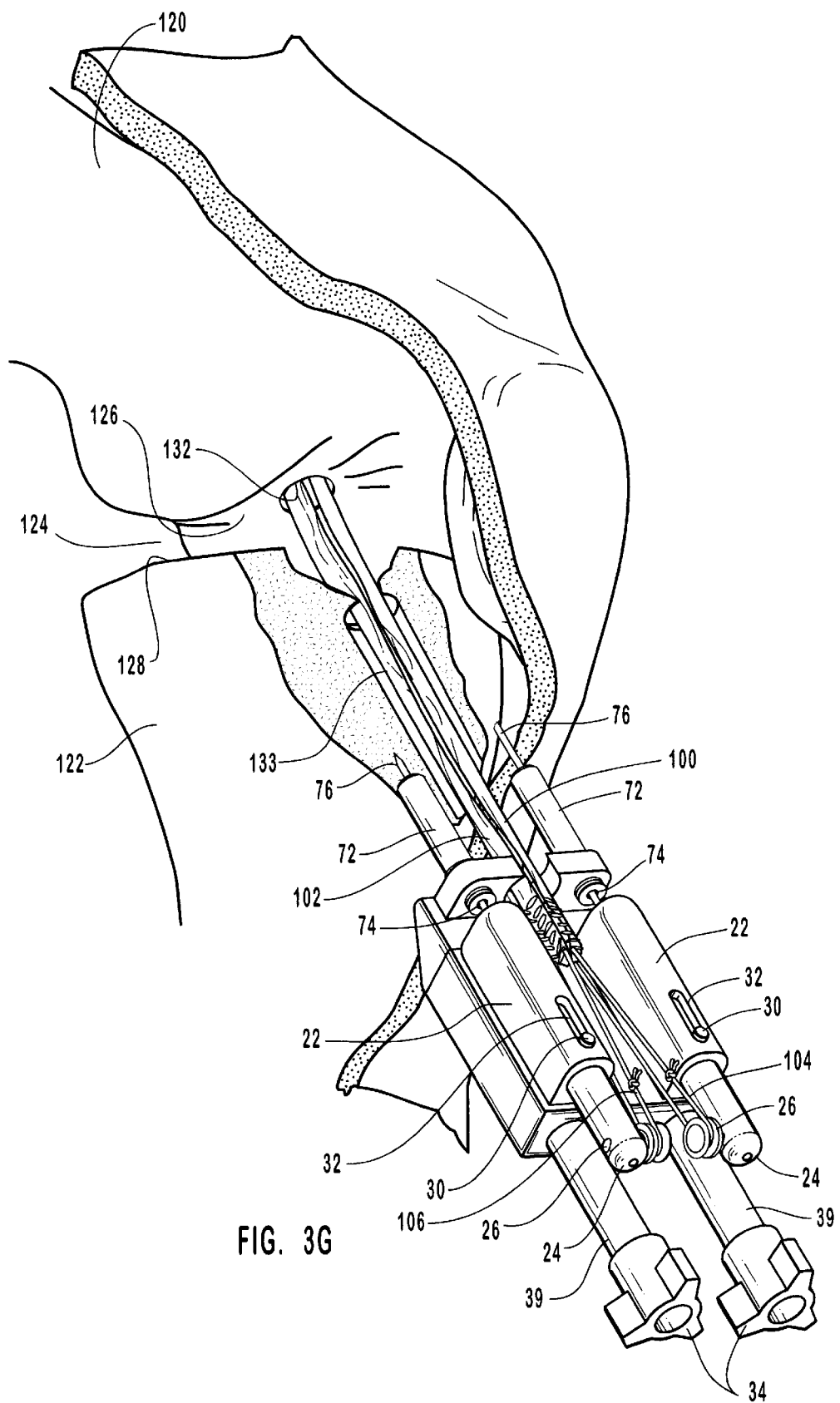

As shown more particularly by comparing FIGS. 3B and 3G, the limb attachment module 66 may include a mating tongue 68 or other protrusion or mechanical feature (not shown) that is able to mate with a corresponding mating hole 70 in the tensioning block or module 16 (FIG. 3F) or other corresponding mechanical feature (not shown). Of course, the features may be reversed so that the mating tongue protrudes from the tensioning module 16 and so that the mating hole is formed within the limb attachment module 66. One of ordinary skill in the art, in light of the teachings herein, will readily appreciate that virtually any desired mechanical mating system may be employed so long as they provide for selective attachment and detachment of the tensioning system 12 from the limb attachment system 14. Of course, it is certainly within the scope of the invention to provide tensioning apparatus in which both the tensioning system 12 and the limb attachment system 14 comprise a single, non-modular unit (not shown).

As more easily seen in FIGS. 1, 2 and 2A, the limb attachment module 66 further includes a pair of pin guides 72, each having a longitudinal guide pin hole 74 therethrough sized so as to accommodate a guide pin 76 (FIG. 3C). When in use, the guide pins 76 are driven, drilled or otherwise pushed into the bone of the patient's limb (as discussed more fully below) in order to slidably attach the limb attachment module 66 to the patient's leg or other limb. In order to utilize the limb attachment module 66 as a template during proper placement of the guide pins 76, the limb attachment module 66 may first be attached to the patient's limb by means of a temporary guide post 78, which is advantageously sized at one end so as to slide into a corresponding hole in the patient's tibia or other bone (FIG. 3B). The other rend of the guide post 78 is advantageously sized so as to pass through a corresponding guide post hole 80 in the center of the front end of the limb attachment module 66. When pressed into the hole in the patient's tibia or other bone, the guide post 78 advantageously holds the limb attachment module 66 in place during placement of the guide pins 76 into the person's tibia or other bone (FIG. 3B).

Once the guide pins 76 have been properly placed, the guide post 78 may be removed so as to allow access to the holes within the tibia and femur and also to allow the limb attachment module 66 to be conveniently slid on and off the guide pins 76 as desired. Even though the limb attachment module 66 is only slidable connected to the guide pins 76, the tensioning device 10 is held in place against the patient's limb by the countervailing tension exerted by the soft tissue graft being tensioned. When conditioning and pre-tensioning of the soft tissue graft has been completed, the soft tissue graft is first secured to the tibia or other bone and then detached from the tensioning device 10. At this point, the tensioning device 10 can be slidably removed from the guide pins 76, which are then also removed from the patient's limb.

Notwithstanding the foregoing, one will readily appreciate, in view of the disclosure herein, that the inventive devices according to the invention are not limited to any particular mechanism for performing the individual and separate tasks of independently tensioning a plurality of soft tissue grafts. The mechanisms described herein are but illustrative and exemplary. For example, the tension loading function could alternatively be provided by a variety of simple scales, such as tension springs, compression springs, torsion springs or electronic transducers. In addition a variety of electronically actuated and measured tensioning devices are certainly within the scope of the invention so long as they are capable of independently tensioning separate soft tissue grafts. Examples include a strain gauge, a rotary gauge, an LVDT and the like.

In addition to conditioning and pre-tensioning individual strands, or separate groups of strands, of a multiple-stranded soft tissue graft, the tensioning device can potentially be used to monitor isometry and measure tension in a single strand of a soft tissue graft. The current design could also be altered in order to incorporate additional adjustable tension applicators that can exert and measure tension in as many stands as a surgeon might choose to include in the soft tissue graft.

An advantage of the inventive tensioning device is the ability to pre-condition the graft after implantation at one end but before fixation of the other end. In the case of an ACL reconstruction procedure, because the soft tissue graft is attached to the tibia near the fixation site, the graft can be tensioned and conditioned by repeatedly flexing and extending the patient's knee under load to remove any laxity or looseness in the graft construct.

The proposed device is advantageously free-standing on the tibia, which can free the surgeon's hands to set knee flexation angle and fix the distal end of the graft while monitoring tension. The device is also able to sustain a desired tensile load on the graft for static tensile loading that will help stretch the graft before final fixation.

III. METHODS FOR INDEPENDENTLY TENSIONING INDIVIDUAL STRANDS OF A SOFT TISSUE GRAFT USED IN JOINT REPAIR PROCEDURES.

An important feature of the present invention is the understanding of the importance of independently conditioning and pre-tensioning each of two or more of the strands, or groups of strands, of a multiple-strand soft tissue graft (e.g., a ham string tissue graft). Thus, it should be understood that the inventive methods disclosed herein may be carried out using any device, either known or which may be developed in the future, that is capable of performing the inventive steps of independently conditioning and pre-tensioning each of two or more strands of a multiple-strand soft tissue graft. Therefore, although the use of the tensioning device 10, as more fully described herein, is preferred, it is merely illustrative and is not intended as a limitation as to the types of apparatus that may be used to perform the inventive methods disclosed herein.

Reference is now made to FIGS. 3A–3L. In a preferred method for carrying out the procedures according to the present invention, two or more strands comprising the soft tissue graft are taken from the patient, such as from the ham strings or patellar tendon. Nevertheless, it is within the scope of the invention to use any semi-tendonosis or gracilis tissue found in the body. In a preferred embodiment, the soft tissue graft will comprise a first soft tissue strand 100 and a second soft tissue strand 102. At some point during the procedure, first graft attachment sutures 104 are attached to the tensioning end of the first soft tissue strand 100 and second graft attachment sutures 106 are attached to the tensioning end of the second soft tissue strand 102.

Either before or after the graft attachment sutures 104 and 106 have been attached to their respective soft tissue strands 100 and 102, the ends of the soft tissue strands 100 and 102 opposite the tensioning ends are attached to an appropriate place on the patient's bone comprising one of the bones of the joint. In the case of surgery to repair a knee joint (e.g., reconstruction of the anterior cruciate ligament), the ends of the soft tissue strands 100 and 102 opposite the tensioning ends are preferably attached to the femur 120. At the end of the conditioning and pre-tensioning procedure, the tensioning ends of the soft tissue strands 100 and 102 are secured to the tibia 122.

As more particularly seen in FIG. 3D, the knee joint 124 comprises, and is defined by, the intersection of the femur 120 and the tibia 122, more particularly the enlarged end 126 of the femur 120 and the enlarged end 128 of the tibia 122. The enlarged end of 128 of the tibia is generally complementary in size and shape to the enlarged end 126 of the femur 120 (for simplicity, we shall hereinafter refer only to the femur 120 and the tibia 122). The knee joint 124 also includes surrounding connective tissue that holds the femur 120 and tibia 122 together so as to normally provide a stable and strong knee joint 124. One of the important components of this connective tissue is the anterior cruciate ligament 130 (ACL), which is a relatively short ligament connected at one end to a lower surface of the femur 120 and at the other end to the opposing surface of the tibia 122. A normal functioning ACL is vital in providing stability and strength of the knee joint 124, particularly for persons such as athletes that engage in physical activity that puts considerable stress onto the knee joint 124.

When the ACL is torn or ruptured, the knee is typically very unstable and weak. During a traumatic event in which the ACL has been severely damaged, other surrounding connective tissue may also be seriously damaged at the same time. If left untreated, a severely damaged ACL may render a person partially or entirely crippled for life. Fortunately, a variety of strategies have been developed to "repair" or reconstruct the ACL, which typically comprises replacing the ACL with a soft tissue graft taken from a different part of the patient's body. In a preferred embodiment according to the present invention, a multiple-strand soft tissue graft, such as a pair of ham strings, may serve as an alternative "ACL" so as to restore the strength and stability of the knee joint 124.

In order to secure the soft tissue graft to either bone constituting the joint (e.g., the femur 120 and the tibia 122 of the knee joint 124), a hole is bored through each of the bones comprising the joint. In the case of reconstruction of the ACL 130, a hole 132 is bored through the femur 120 and a corresponding hole 133 is bored through the tibia 122 using known surgical procedures. The strands of the soft tissue graft, such as first and second soft tissue strands 100 and 102, are first drawn through the holes 132 and 133 bored through the femur 120 and tibia 122, respectively, according to known surgical procedures. Thereafter, the ends of the first and second soft tissue strands 100 and 102 opposite the tensioning ends are attached to the femur 120 according to known surgical procedures. The graft attachment sutures 104 and 106 are attached to the tensioning ends of the first and second soft tissue strands 100 and 102, respectively, at an appropriate point during the implantation procedure using known methods, typically prior to passing the first and second soft tissue strands 100 and 102 through the holes 132 and 133 of the femur 120 and tibia 122, respectively, and prior to attaching the first and second soft tissue strands 100 and 102 to the femur 120.

Once the first and second soft tissue strands 100 and 102 have been passed through holes 132 and 133, securely mounted to the femur 120, and attached to first and second graft attachment sutures 104 and 106, respectively, they are ready for conditioning and pre-tensioning. In order to properly "condition" each of first and second soft tissue strands 100 and 102, a minimum tensile load is separately applied to each of the soft tissue strands 100 and 102 for an appropriate period of time in order to prevent further stretching or relaxation of the soft tissue strands after anchorage to the tibia 122. In addition, after conditioning, but before securing the first and second soft tissue strands 100 and 102 to the tibia 122, it will generally be desirable to further pre-tension each of the soft tissue strands 100 and 102 to a desired tensile load in order to ensure that each contributes the same, or substantially the same, level of stability and strengthening force to the knee joint 124. In this way, each strand is able to advantageously contribute to the strength and stability of the overall graft.

In a preferred embodiment, the steps of separately and independently conditioning and pre-tensioning each of the first and second soft tissue strands 100 and 102 is advantageously carried out using the tensioning device 10 depicted in FIGS. 1 and 2, and described in detail above. As more particularly shown sequentially in FIGS. 3A–3L, the tensioning device 10 is utilized as follows, with the guide pins 76 of the tensioning device 10 first being properly placed and secured to the tibia 122 prior to passing the soft tissue graft through the holes 132 and 133 in the femur 120 and tibia 122, respectively, and prior to attaching one end of the graft to the femur 120.

First, the holes 132 and 133 through the femur and tibia 122, respectively, are formed using standard surgical techniques (e.g., using a drill). In conjunction with this, an access hole 134 through the flesh in the vicinity of the hole 133 through the tibia 122 is provided (FIG. 3A). Second, the limb attachment block or module 66 is secured to the tibia 122 by means of sliding the guide post 78 into the hole 133 through the tibia 122, as described above (FIG. 3B). Third, the guide pins 76 are driven, drilled or otherwise attached to the tibia 122 in the appropriate location using the limb attachment module 66 as a template, more particularly, the pin guides 72 and associated guide pin holes 74 of the limb attachment module 66 (FIG. 3C). In a preferred embodiment, the ends of the guide pins 76 will be provided with a tip that has a cutting surface so as to be self-tapping and able to bore into the tibia 122 by means of a drill (not shown). Once the guide pins 76 have been secured to the tibia 122, the guide post 78 and limb attachment module 66 are removed.

With the guide pins 76 in place following removal of the guide post 78 and limb attachment module 66, the first and second soft tissue strands 100 and 102 comprising the graft, which are attached to first and second graft attachment sutures 104 and 106, respectively, are inserted through the access hole 134 (FIG. 3D). The ends of the soft tissue strands 100 and 102 opposite to where the graft attachment sutures 104 and 106 are attached are fed through the holes 132 and 133 of the femur 120 and tibia 122, respectively, and attached to the femur 120 using known surgical procedures (not shown). Examples include screws, pins, staples, posts and other anchor devices known and used in the art.

Thereafter, the limb attachment module 66 of the limb attachment system 14 is slidably attached to the guide pins 76 by sliding each of the pin guides 72 over their respective guide pins 76 until the limb attachment module 66 makes abutment with the patient's leg (FIG. 3E). The tensioning module 16 of the tensioning system 12 is then attached to the limb attachment module 66 by inserting the mating tongue 68 of the limb attachment module 66 through the mating hole 70 of the tensioning module 16 (FIG. 3F). Finally, each of the graft attachment sutures 104 and 106 attached to the soft tissue graft strands 100 and 102, respectively, is attached to a respective adjustable tension applicator 18 or 20 (FIG. 3G). The tensioning device 10 is now ready for use in separately and independently conditioning and pre-tensioning each of the first and second soft tissue strands 100 and 102.

The tension adjustment knobs 34 of each of first and second adjustable tension applicators 18 and 20 are separately operated as desired to independently apply a desired tensile load onto each of the first and second soft tissue strands 100 and 102, respectively. The magnitude of the tensile load being applied to each soft tissue strand may be measured by the displacement of each tension indicator pole 30 relative to its respective tension indicator slot 32, particularly by referencing the location of each tension indicator pole 30 in relation to corresponding graduations 33 on the side of the corresponding tension indicator slot 32. It may be desirable in some cases to tension each soft tissue strand with the same tensile load. In other cases, particularly where the strands of the soft tissue graft are of different cross-sectional thicknesses, it may be necessary or desirable to applied different tensile loads to each soft tissue strand. In general, it may be necessary to apply greater tensile loads to thicker soft tissue strands. Conversely, thinner soft tissue strands may require a lower tensile load to achieve adequate conditioning.

Figure 3H:
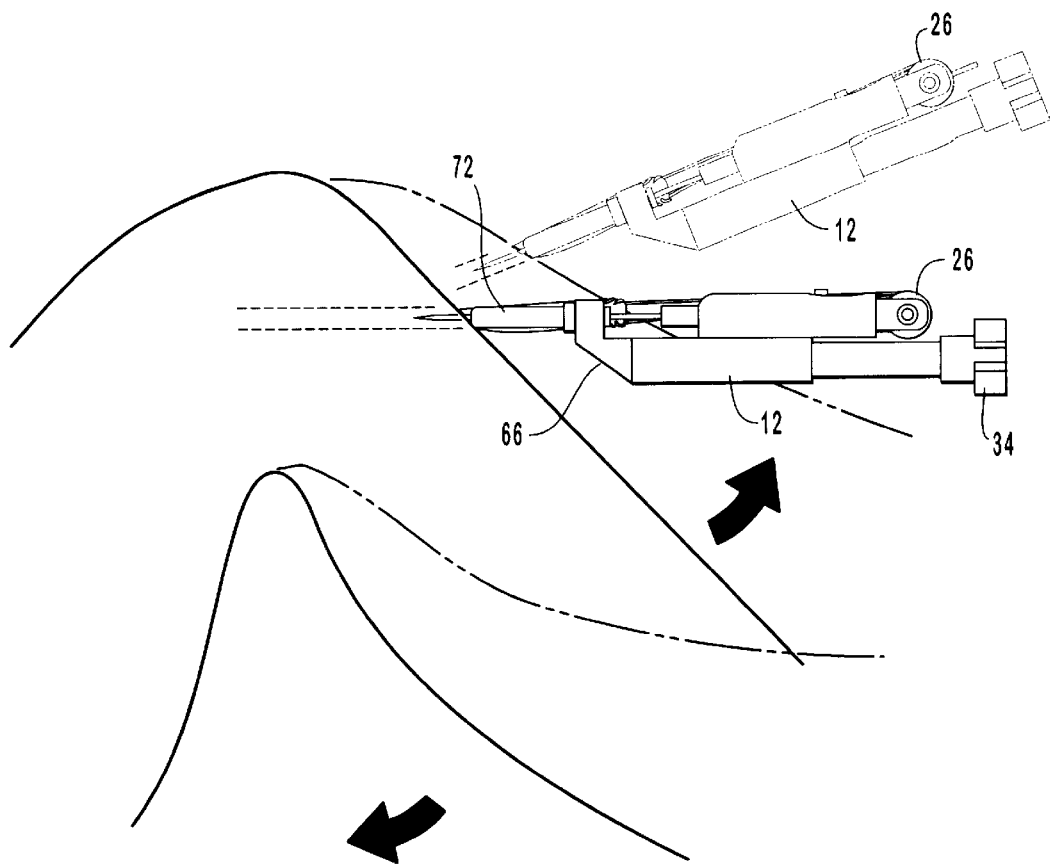
Figure 3I:
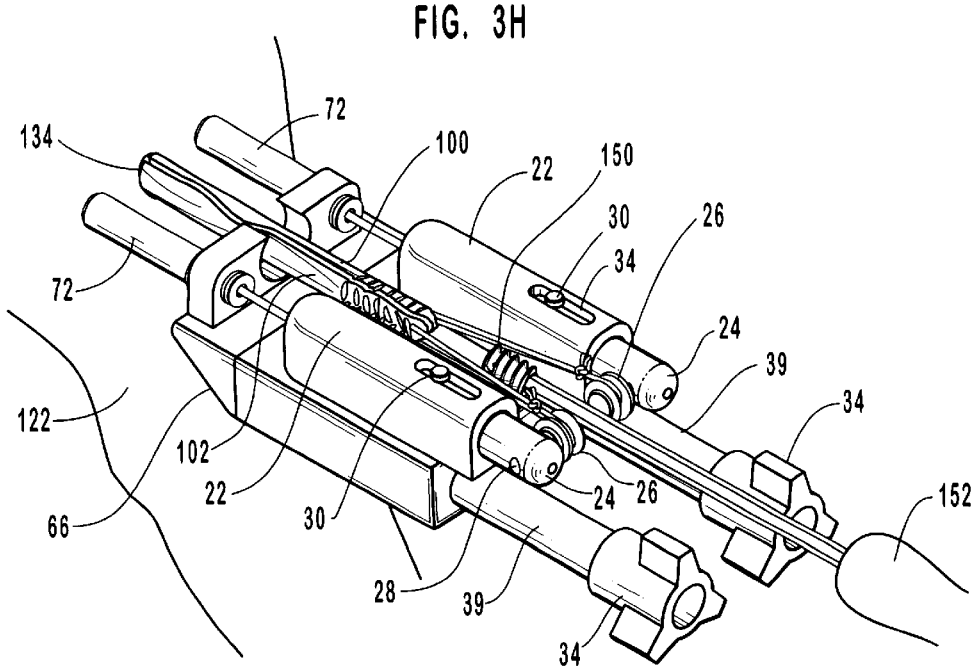
Figure 4A:
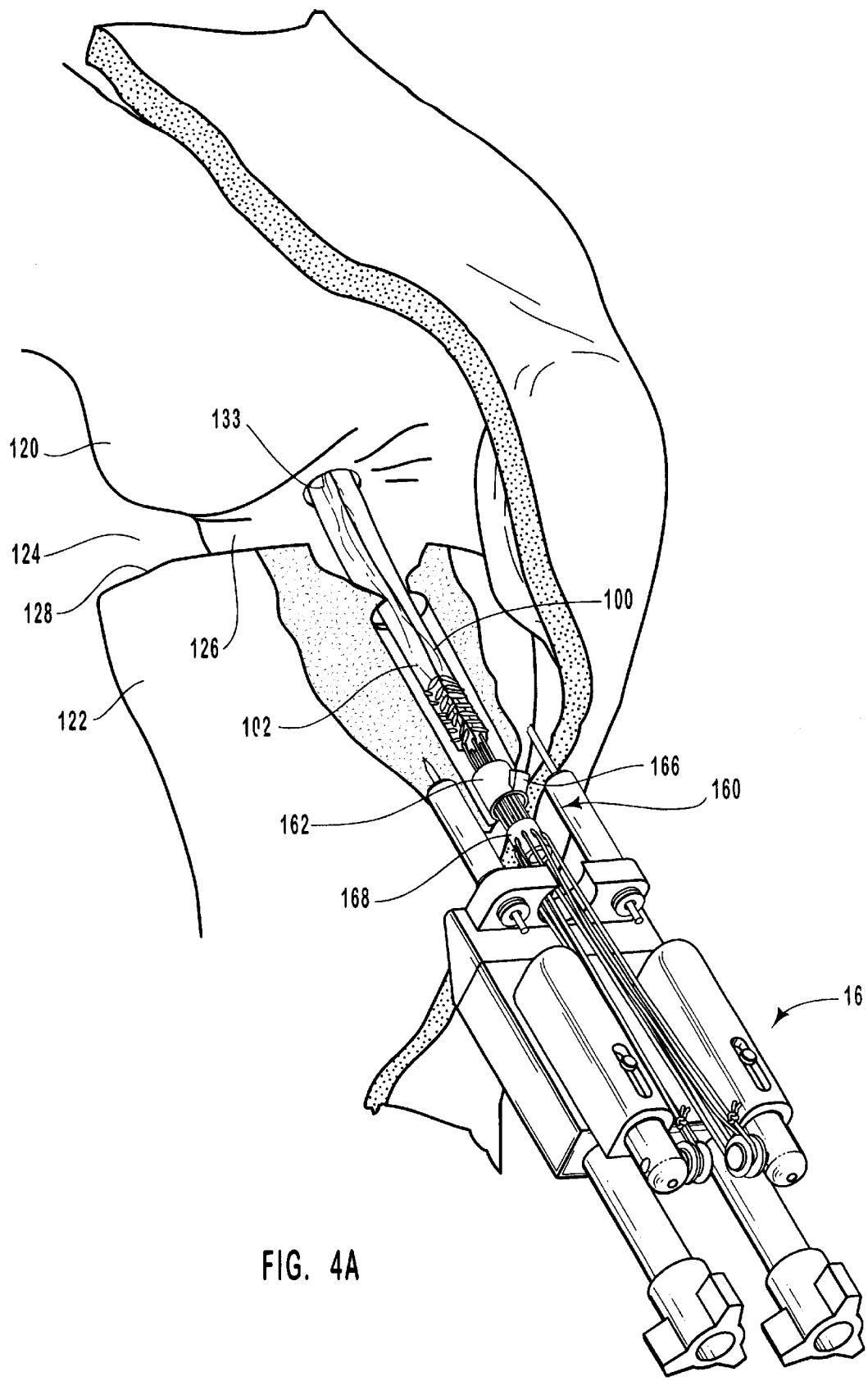
FIGS. 4A–4C alternatively shows a soft tissue graft being secured to a bone using an implantable anchor device instead of, or in addition to, an interference screw.
Figure 4B:
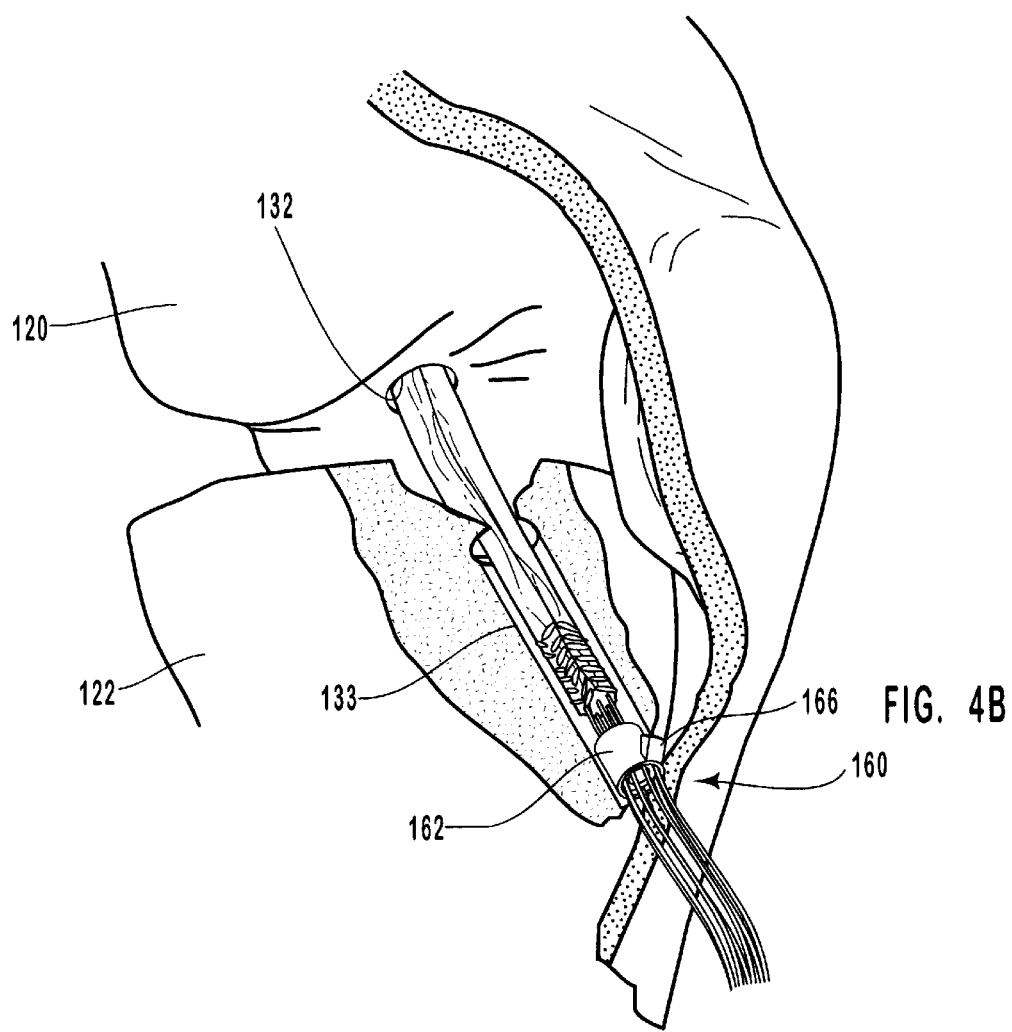
Figure 4C:
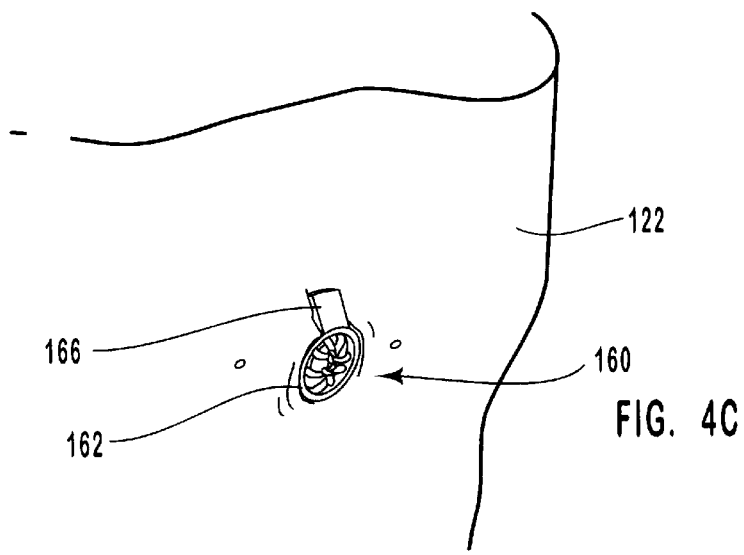

In order to test whether the strands of the soft tissue graft have been adequately conditioned, it may be desirable to "cycle" the leg by flexing and then extending the leg or other limb through a desired radial distance of, for example, 90° (FIG. 3H). The cycling process may itself assist in conditioning the soft tissue graft. If, after cycling, the soft tissue graft has loosened, or if the joint is not adequately stable, further adjustments to the tension adjustment knobs 34 maybe required so as to increase the tensile load applied to one or more of the soft tissue graft strands 100 and 102 to ensure proper conditioning and pre-tensioning of the soft tissue graft. The process of alternatively tightening the tension adjustment knobs 34 and cycling the knee joint 124 may be repeated as needed until losses in joint strength and stability become negligible. At this point, proper conditioning and pre-tensioning of the individual strands of the soft tissue graft have been achieved.

It should be understood that even though the tensioning pistons 24 are essentially immobile, with the cylinder modules 22 doing most, if not all, of the movement as the tension adjustment knobs 34 are tightened, some movement of the tensioning pistons 24 may be observed due to stretching of one or more of the soft tissue strands 100 and 102. This movement, however, will typically be only a few millimeters or less. In any event, the amount of force that is independently applied to each of soft tissue strands 100 and 102 is independent of the movement of the tensioning pistons 24, thus negating any effect of unequal stretching or movement of the soft tissue strands 100 and 102. On the other hand, devices that attempt to condition and pre-tension the soft tissue graft with a single, undivided tensile load, are incapable of accounting for unequal stretching or movement of the soft tissue strands, thus resulting in unevenly conditioned and/or pre-tensioned strands. Thus, the methods and apparatus according to the present invention are a tremendous advancement in the art of preparing soft tissue grafts for use in joint repair surgery.

After the soft tissue strands 100 and 102 of the soft tissue graft have been properly conditioned and pre-tensioned, they are advantageously anchored or otherwise attached to the tibia 122 in order to maintain the desired amount of pre-tensioning. This may be accomplished, for example, by means of an interference screw 150 (FIG. 31). The interference screw 150 may be driven into the hole 132 in the tibia 122 by means of, e.g., a specially adapted screw driver 152. Alternatively, the graft may be anchored to the tibia 122 by means of an implantable anchor device 160, discussed more fully below.

After securing the soft tissue strands 100 and 102 of the soft tissue graft to the tibia 122 by means of the interference screw 150, the tensioning device 10 is removed by cutting or otherwise separating the sutures 104 and 106 from the suture attachment wheels 26 and then sliding the tensioning device 10 off of the guide pins 76 (FIG. 3J). Thereafter, the guide pins 76 are removed from the patient's tibia by known surgical procedures, such as by means of a "needle holder" (not shown).

The ends of the soft tissue strands 100 and 102 of the soft tissue graft are thereafter secured to the outside surface of the tibia 122 by standard surgical procedures, such as by means of a spiked washer, staple or post. FIG. 3K depicts a spiked washer 154 used to secure the ends of the soft tissue graft tot he tibia 122. Finally, the end of the soft graft beyond the spiked washer 154 or other attachment means is trimmed to remove the graft attachment sutures 104 and 106 (FIG. 3L) using standard cutting apparatus (e.g., by means of a scalpel or surgical scissors, not shown).

Figure 5:
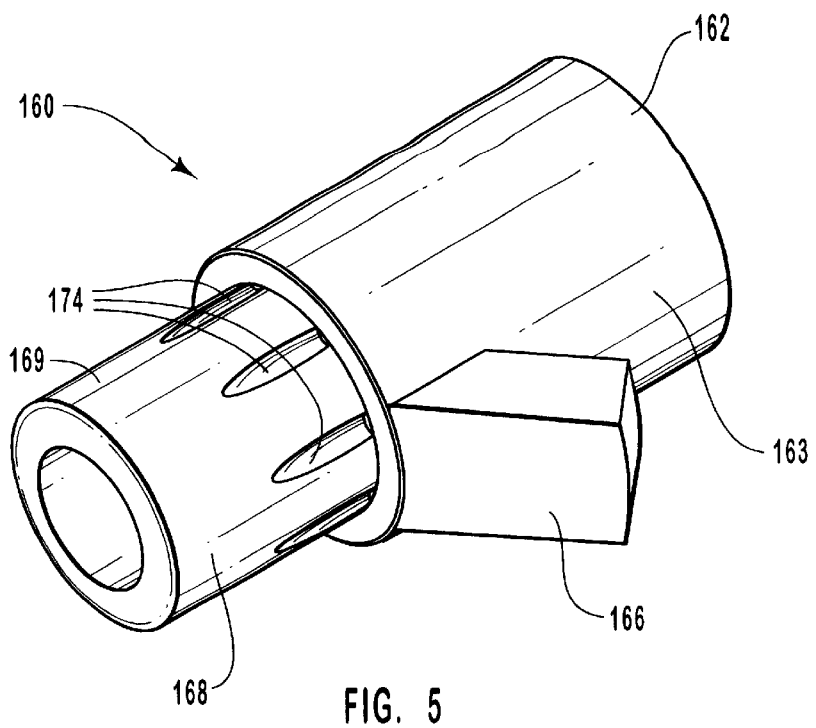
FIG. 5 is a perspective view of an anchor device according to the invention that allows for tensioning of sutures while in a non-deployed state and which locks the sutures upon deployment of the anchor device.
Figure 6:
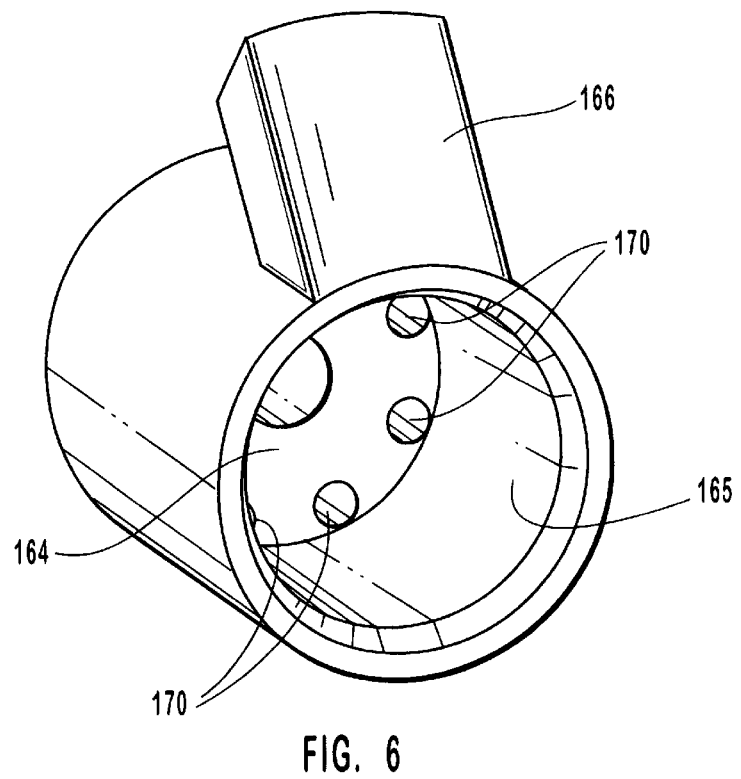
FIG. 6 is a perspective view of the outer sheath of the anchor device of FIG. 5.
Figure 7:
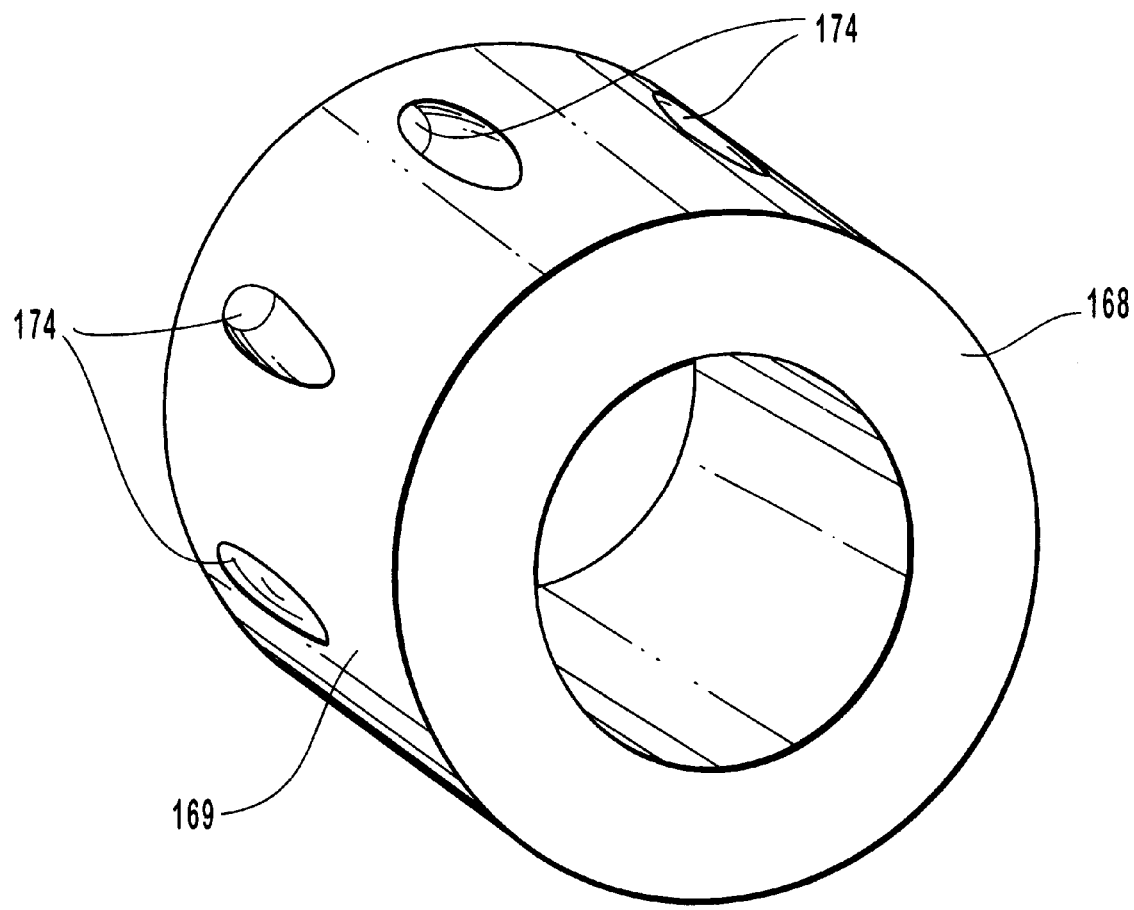
FIG. 7 is a perspective view of the locking core of the anchor device of FIG. 5.

In an alternative embodiment, a novel implantable anchor device 160 as depicted in FIGS. 5–7 according to the present invention maybe employed to secure the soft tissue graft to the bone. The inventive anchor device 160 includes a generally cylindrical outer sheath 162 having a cylindrical outer wall 163, a generally cylindrical bore 164 therethrough, defining an inner sheath wall 165, and a bone engagement lip 166 (FIG. 6). A corresponding locking core or shaft 168 is used to lock the sutures into place once the conditioning and pre-tensioning procedure has been completed (FIG. 7).

The circumference of the outer wall 163 of the outer sheath 162 is selected to fit within a corresponding hole 133 bored through the tibia 122 or other bone. The bottom part of the outer sheath 162, or the part of the outer sheath 162 which faces the bone, includes a plurality of suture holes 170 disposed near the outer edge of the outer sheet 162 adjacent to the cylindrical outer wall 163. The suture holes 170 permit passage therethrough of individual suture strands attached to the strands of the soft tissue graft. When the anchor device 160 is placed into the hole 133 within the tibia 122 or other bone, the engagement lip 100 or other protrusion overlaps the outer surface of the bone, thus acting as a stop. The tension exerted inwardly by the soft tissue graft onto the sutures effectively pulls the engagement lip 166 or other protrusion against the bone, thereby reliably locking the anchor device 160 against the bone.

The locking core 168 is capable of sliding into and out of the outer sheath 162, but has a slightly tapered outer wall 169 so that it can form an increasingly tighter press fit with the inner wall 165 of the outer sheath 162 as it is pressed or forced into the sheath 162. The locking core 168 is preferably hollow and includes suture passages 174 passing through the bottom edge nearest, and corresponding to, the suture holes 170 of the outer sheath 162. The suture passages 174 pass approximately longitudinally through the locking core 168 but at an angle so that they exit through the outer wall 169 of the locking core 168 rather than the top edge, or the edge facing away from the outer sheath 162. In this way, the sutures attached to the soft tissue graft will pass through the locking core 168 in a manner so as that, when the locking core is deployed, the sutures will be tightly pinched between the outer wall 169 of the locking core 168 and the inner wall 165 of the outer sheath 162. This pinching action prevents the sutures from slipping back into the bone hole, thus maintaining the desired tension on the sutures and associated soft tissue graft strands after conditioning and pre-tensioning of the individual graft strands, as described more fully above. Prior to deployment of the locking core 168, the sutures are free to slide between the outer sheath 162 and the locking core 168, which allows an appropriate tensioning apparatus, such as the tensioning device 10, to increase or decrease the tensile load applied to the soft tissue graft strands, as desired.

IV. SUMMARY.

In conclusion, the invention provides apparatus and methods for independently conditioning and pre-tensioning individual soft tissue graft strands, such as a pair of hamstrings used in an ACL reconstruction procedure.

The invention additionally provides apparatus and methods for conditioning and pre-tensioning individual grafts strands so that each graft strand may substantially contribute to the overall strength and stability of the repaired joint.

The invention yet provides apparatus and methods for conditioning and pre-tensioning individual graft strands that can equalize the otherwise unequal conditioning and pre-tension of the individual graft strands that might occur, for example, by strands of different diameters or stiffnesses, or through inadvertent or unavoidable surgical error, such as failure to tie the sutures in a manner that each graft strand is tensioned equally.

The invention also provides an improved anchor device that can be used in conjunction with the foregoing apparatus and methods and which allows for the independent tensioning of sutures attached to individual soft tissue graft strands and which can be manipulated after independently tensioning the sutures so as to subsequently lock the sutures in place and thereby reliably secure each of the soft tissue graft strands to the bone at a desired tension.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A tensioning device for use in joint repair surgery comprising:
    means for removably attaching the tensioning device to a person's limb;
    first tensioning means for selectively increasing or decreasing a first tensile load applied to a first strand of a soft tissue graft;
    second tensioning means for selectively increasing or decreasing a second tensile load applied to a second strand of a soft tissue graft independently from the first tensile load applied to the first soft tissue graft strand; and
    a suture attachment wheel rotatably connected to at least one of the first or second tensioning means so that when a suture strand is looped around the suture attachment wheel equal tension is applied to each side of the looped suture strand.

2. A tensioning device as defined in claim 1, wherein the means for removably attaching the tensioning device to a person's limb includes at least one hollow pin guide that is sized and configured so as to slidably attach to a corresponding guide pin affixed to the person's limb so that the tensioning device can be selectively attached and detached from the person's limb while the guide pin remains affixed to the person's limb.

3. A tensioning device as defined in claim 1, wherein each of the first and second tensioning means includes an adjustable tensioning apparatus having:
    a tensioning piston adapted to receive and secure thereto one or more sutures attached to at least one soft tissue graft strand;
    a hollow cylinder slidably disposed around at least a portion of the tensioning piston;
    a spring disposed within the hollow cylinder and communicating between the hollow cylinder and tensioning piston so as to increase the tensile load applied by the tensioning piston onto the soft tissue graft strand as the spring is compressed; and
    a tensioning bolt in threaded communication with the hollow cylinder in a manner so that selective rotation of the tensioning bolt causes a corresponding movement of the hollow cylinder relative to the tensioning bolt.

4. A tensioning device as defined in claim 3, wherein each tensioning piston includes a suture attachment wheel rotatably attached thereto.

5. A tensioning device as defined in claim 3, wherein the tensioning piston includes at least one of a slot, posts, hole or ridge configured so as to assist in securing at least one suture to the tensioning piston.

6. A tensioning device as defined in claim 3, further including gauge means for measuring the tensile load applied by at least one of the first and second tensioning means.

7. A tensioning device as defined in claim 6, wherein the gauge means includes a plurality of graduations disposed on an outer surface of the hollow cylinder.

8. A tensioning device as defined in claim 1, further including a temporary guide post sized and configured at one end to be received within a corresponding hole in the person's limb and sized and configured at an opposite end to be removably attached to a guide post hole within the attachment means.

9. A tensioning device for use in joint repair surgery comprising:
    an attachment portion comprising a plurality of hollow pin guides, each hollow pin guide being configured to slidably receive a corresponding guide pin affixed to a person's limb so that the tensioning device can be selectively attached and detached from the person's limb while the guide pin remains affixed to the person's limb; and
    a tensioning portion associated with the attachment portion and configured to independently apply a desired tensile load to each of at least two separate strands of a soft tissue graft, the tensioning portion comprising:
        a first adjustable tensioning apparatus configured so as to selectively increase or decrease a first tensile load applied to a first strand of a soft tissue graft; and
        a second adjustable tensioning apparatus configured so as selectively increase or decrease a second tensile load applied to a second strand of the soft tissue graft independently from the tensile load applied to the first strand of the soft tissue graft.

10. A tensioning device as defined in claim 9, wherein the attachment portion and the tensioning portion are removably attached to each other such that they may be selectively attached and detached.

11. A tensioning device as defined in claim 9, wherein the attachment portion and the tensioning portion are permanently affixed to each other.

12. A method for conditioning and pre-tensioning a multiple-stranded soft tissue graft during joint repair surgery, comprising:
    providing a multiple-stranded soft tissue graft including at least two soft tissue strands for use in repairing a patient's joint;
    attaching a first end of each soft tissue strand to a first bone associated with the patient's joint while leaving a free end of each soft tissue strand to enable subsequent conditioning and pre-tensioning of each soft tissue strand;
    applying a first tensile load to the free end of a first soft tissue strand;
    applying a second tensile load to the free end of a second soft tissue strand independently from the first tensile load applied to the first soft tissue strand;

conditioning the soft tissue strands by repeatedly flexing and extending the patient's joint; and independently adjusting the tensile loads applied to the free ends of each of the first and second soft tissue strands so as to apply a desired final tensile load to each of the first and second soft tissue strands in preparation for securing the first and second soft tissue strands to a second bone associated with the patient's joint.

13. A method as defined in claim 12, further including the step of attaching at least one suture strand to the free end of each soft tissue strand, wherein a tensile load is applied to each soft tissue strand by means of applying the tensile load to the at least one suture attached to the soft tissue strand.

14. A method as defined in claim 12, wherein the multiple-stranded soft tissue graft comprises at least two ham string strands and wherein the method is part of a procedure for reconstructing the patient's anterior cruciate ligament.

15. A method as defined in claim 12, wherein the multiple-stranded soft tissue graft comprises at least two patellar tendon strands and wherein the method is part of a procedure for reconstructing the patient's anterior cruciate ligament.

16. A method as defined in claim 12, wherein the method further includes repeating the acts of conditioning the soft tissue strands and independently adjusting the tensile loads applied to the free ends of each of the first and second soft tissue strands until the patient's joint has a desired level of stability.

17. A method as defined in claim 12, further including the step of securing the free ends of the soft tissue strands to the second bone associated with the patient's joint.

18. A method as defined in claim 17, wherein the multiple-stranded soft tissue graft is secured to the second bone by means of an anchor device that includes an outer sheath configured to fit within a hole in the second bone, a lip associated with the outer sheath and configured to overlap the second bone in order to limit penetration of the outer sheath through the hole in the second bone, and an inner core slidably disposed within the outer sheath.

19. A method as defined in claim 17, wherein the free ends of the soft tissue strands are secured within a hole in the second bone by inserting an interference screw into the hole.

20. A tensioning device for use in joint repair surgery comprising:

a tensioning block comprising a plurality of independently adjustable tension applicators, each tension applicator comprising:

a hollow cylinder slidably connected to the tensioning block so as to be selectively advanced or withdrawn relative to a joint being repaired when the tensioning device is in use, a tensioning piston slidably received within the hollow cylinder and adapted to receive and secure one or more suture strands attached to a first soft tissue graft strand;

a tensioning bolt in threaded communication with the hollow cylinder in a manner so that selective rotation of the tensioning bolt causes corresponding movement of the hollow cylinder relative to the tensioning block; and a biasing spring disposed within the hollow cylinder in a manner so as to communicate between the hollow cylinder and the tensioning piston, wherein compressing the biasing spring increases a tensile load applied by the tensioning piston to one or more suture strands attached thereto and decompressing the biasing spring decreases the tensile load.

21. A tensioning device as defined in claim 20, further comprising a suture attachment wheel rotatably connected to the tensioning piston so that, when a suture strand is looped around the suture attachment wheel, equal tension is applied by the tensioning piston to each side of the looped suture strand.

\* \* \* \* \*

UNITED STATES PATENT AND TRADEMARK OFFICE
CERTIFICATE OF CORRECTION

PATENT NO. : 6,679,889 B1
DATED : January 20, 2004
INVENTOR(S) : Hugh S. West, Jr. and John R. West It is certified that error appears in the above-identified patent and that said Letters Patent is hereby corrected as shown below:

Column 1,
Line 16, change "ham string" to -- hamstring --

Column 3,
Line 25, after "importance" insert -- of --
Line 30, after "time" insert -- in --
Line 44, change "reliable" to -- reliably --

Column 4,
Line 2, change "are" to -- is --

Column 5,
Line 53, change "ham strings" to -- hamstrings --

Column 7,
Line 3, after "through" insert -- the --
Line 12, before "cylindrical" insert -- the --

Column 8,
Line 57, change "but" to -- and --
Line 58, change "ham strings" to -- hamstrings --

Column 9,
Line 11, after "tearing" change "or" to -- of --
Line 15, change "born" to -- borne --
Line 30, change "ham strings" to -- hamstrings --
Line 66, change "tensioning" to -- tension --

Column 13,
Line 14, change "rend" to -- end --
Line 26, change "slidable" to -- slidably --

Column 14,
Lines 31-32, change "ham strings" to -- hamstrings --
Line 57, after "end" delete "of"

Column 15,
Line 15, change "ham strings" to -- hamstrings --

UNITED STATES PATENT AND TRADEMARK OFFICE
CERTIFICATE OF CORRECTION

PATENT NO. : 6,679,889 B1
DATED : January 20, 2004
INVENTOR(S) : Hugh S. West, Jr. and John R. West It is certified that error appears in the above-identified patent and that said Letters Patent is hereby corrected as shown below:

Column 16,
Line 67, change "applied" to -- apply --

Column 18,
Line 1, change "tot he" to -- to the --

Column 21,
Line 15, change "ham string" to -- hamstring --

Signed and Sealed this

Sixth Day of July, 2004

JON W. DUDAS
*Acting Director of the United States Patent and Trademark Office*